United States Patent
Berger et al.

(10) Patent No.: US 11,846,036 B2
(45) Date of Patent: Dec. 19, 2023

(54) ELECTROLYTE FOR THE CYANIDE-FREE DEPOSITION OF SILVER

(71) Applicant: Umicore Galvanotechnik GmbH, Schwaebisch Gmuend (DE)

(72) Inventors: Sascha Berger, Schwaebisch Gmuend (DE); Klaus Bronder, Waeschenbeuren (DE); Mario Tomazzoni, Schwaebisch Gmuend (DE); Uwe Manz, Moegglingen (DE)

(73) Assignee: Umicore Galvanotechnik GmbH, Schwaebisch Gmuend (DE)

( * ) Notice: Subject to any disclaimer, the term of this patent is extended or adjusted under 35 U.S.C. 154(b) by 340 days.

(21) Appl. No.: 17/260,090

(22) PCT Filed: Aug. 20, 2019

(86) PCT No.: PCT/EP2019/072275
§ 371 (c)(1),
(2) Date: Jan. 13, 2021

(87) PCT Pub. No.: WO2020/038948
PCT Pub. Date: Feb. 27, 2020

(65) Prior Publication Data
US 2022/0205122 A1  Jun. 30, 2022

(30) Foreign Application Priority Data

Aug. 21, 2018 (DE) ...................... 10 2018 120 357.8
Mar. 8, 2019 (DE) ...................... 10 2019 106 004.4

(51) Int. Cl.
| | |
|---|---|
| C25D 3/46 | (2006.01) |
| C25D 3/64 | (2006.01) |
| C07D 233/74 | (2006.01) |
| C25D 17/10 | (2006.01) |
| C25D 21/12 | (2006.01) |

(52) U.S. Cl.
CPC ............. C25D 3/46 (2013.01); C07D 233/74 (2013.01); C25D 3/64 (2013.01); C25D 17/10 (2013.01); C25D 21/12 (2013.01)

(58) Field of Classification Search
None
See application file for complete search history.

(56) References Cited

U.S. PATENT DOCUMENTS

| | | | |
|---|---|---|---|
| 5,601,696 A | 2/1997 | Asakawa | |
| 6,251,249 B1 * | 6/2001 | Chevalier | C25D 3/52 205/267 |
| 6,620,304 B1 * | 9/2003 | Hoffacker | C25D 3/48 205/255 |
| 2005/0183961 A1 | 8/2005 | Morrissey | |
| 2011/0062030 A1 | 3/2011 | Lippert | |
| 2012/0067733 A1 | 3/2012 | Zhang-Beglinger | |
| 2012/0067735 A1 | 3/2012 | Clauss | |
| 2016/0122890 A1 | 5/2016 | Schaefer | |

FOREIGN PATENT DOCUMENTS

| | | |
|---|---|---|
| CN | 102168290 | 8/2011 |
| CN | 102268701 B | 10/2013 |
| CN | 103806060 | 5/2014 |
| CN | 104342726 | 2/2015 |
| CN | 105506683 | 4/2016 |
| CN | 107841771 | 3/2018 |
| EP | 0225422 | 6/1987 |
| EP | 2551382 | 1/2013 |
| EP | 2634293 | 9/2013 |
| JP | H11302893 | 11/1999 |
| JP | 2012092434 | 5/2012 |
| JP | 2018009227 | 1/2018 |
| WO | 2005083156 | 9/2005 |
| WO | 2008043528 | 4/2008 |
| WO | 2015018654 | 2/2015 |
| WO | 2017067985 | 4/2017 |

OTHER PUBLICATIONS

Zhao, CN 102268701 A, machine translation (Year: 2011).*
Written Opinion received in PCT/EP2019/072275, dated Nov. 25, 2019.
International Search Report received in PCT/EP2019/072275, dated Nov. 25, 2019.
Beyer-Walter, "Lehrbuch der Organischen Chemie", 1991, pp. 496, 497, 575-577, 784, 785, Publisher: S. Hirzel Verlag Stuttgart, 22.
Cobley, et al., "The use of Insoluble Anodes in Acid Sulphate Copper Electrodeposition Solutions", 2001, pp. 112-119, vol. 79, No. 3, Publisher: Trans IMF.
"Anodizing of aluminium and its alloys—Measurement of specular reflectance and specular gloss of anodic oxidation coatings at angles . . . ", , vol. ISO 7668:2018(E), Publisher: International Standard ISO, 3rd ed.
Kanani, N, Publisher: Galvanotechnik; Hanser Verlag, Mnchen Wien, 2000; Seite 84 ff.
Leuze-Verlag, "Prfung von funktionellen metallischen Schichten, Kap. 4.3: Glanz- und Reflexionsmessung an Oberflchen, Saulgau", 1997, pp. 117-126, vol. 1, Publisher: Schriftenreihe Galvanotechnik und Oberflchenbehandlung.
Office Action received in SG11202013166Y dated Jul. 24, 2022.
Office Action received in JP2021535276 dated Jun. 19, 2023 (Machine Translation).

* cited by examiner

Primary Examiner — Wojciech Haske
(74) Attorney, Agent, or Firm — Suzannah K. Sundby, Esq.; Canady + Lortz LLP

(57) ABSTRACT

The present invention relates to an electrolyte and to a method for the electrolytic deposition of silver coatings and silver alloy coatings. The electrolyte according to the invention is cyanide-free, storage-stable and ensures the deposition of high-gloss, brilliant and white silver and silver alloy layers for technical and decorative applications.

12 Claims, 3 Drawing Sheets

ELECTROLYTE FOR THE CYANIDE-FREE DEPOSITION OF SILVER

The present invention relates to an electrolyte and to a method for the electrolytic deposition of silver coatings and silver alloy coatings. The electrolyte according to the invention is cyanide-free, storage-stable and ensures the deposition of glossy, brilliant and white silver layers and silver alloy layers for technical and decorative applications.

Industrially, silver is often galvanically deposited from cyanide-based electrolytes. However, there is a need for cyanide-free electrolytes due to the toxicity of cyanide. In currently known cyanide-free silver electrolytes, silver is generally used in the form of an organic complex, or the organic silver complex is formed in situ. In many of these cyanide-free silver electrolytes, bath stability is insufficient. Furthermore, the deposited silver coatings are frequently not sufficiently white and/or the gloss is insufficient. There is therefore a continuing need for the development of stable, cyanide-free silver electrolytes for technical and decorative applications.

Hydantoin derivatives are frequently used as organic complexing agents for silver. Thus, US 2005/0183961 A1 discloses a galvanic bath for the deposition of silver. Here, silver is used in the form of a non-precipitating, water-soluble salt. The organic complexing agent used is 5,5-dimethylhydantoin or a derivative thereof, and pyridyl derivatives serve as brighteners. The baths have a pH of 9 to 13. It is particularly advantageous if the bath contains both 2,2-dipyridyl and a substituted pyridine compound as brightener and additionally a wetting agent. Advantageous wetting agents are substituted glycine derivatives, which are known commercially as Hamposyl® and sulfonated naphthalene-formaldehyde condensates, which are commercially available as Blanco N or Rhodacal N. Hamposyl® is composed of N-acyl sarcosinates, i.e., condensation products of fatty acid acyl residues and N-methylglycine (sarcosine). Silver coatings deposited with these baths are white and glossy to high-gloss.

U.S. Pat. No. 5,601,696 discloses a galvanic bath for the deposition of silver and a method for the deposition of silver using this bath. The bath comprises silver salts of inorganic acids, for example silver nitrate and silver oxide, and a complexing agent which is a hydantoin derivative. Furthermore, the bath may optionally contain a brightening agent. These are at least one organic sulfur compound which contains an SH group or a carboxyl group, a sulfur-containing amino acid or sulfite ions. Mention is made, as examples of brightening agents, of thiosalicylic acid, thiamine hydrochloride, thiamine nitrate and potassium sulfite. The bath may further contain conducting salts. These are preferably inorganic salts such as potassium chloride, potassium formate and carboxylates. The pH of the bath is between 8 and 13, the bath temperature during deposition is 30° C. to 90° C., and the current density is between 1 and 150 A/dm2, depending on the application. The baths described in U.S. Pat. No. 5,601,696 give glossy silver layers and can be used for up to three passes.

WO 2008/043528 A2 discloses a cyanide-free electrolyte composition for the deposition of a silver layer or silver alloy layer which has a silver ion source, a sulfonic acid or a derivative of a sulfonic acid, a wetting agent and a hydantoin derivative. The electrolyte composition serves for the deposition of crack-free and ductile silver layers and silver alloy layers. The silver ion source used is at least one silver salt of a sulfonic acid. Optionally, further silver ion sources selected from silver oxide, silver nitrate and silver sulfate may be present. If silver alloy layers are to be deposited, corresponding sources of alloy metal ions are used, advantageously sulfonic acid salts, oxides, nitrates or sulfates. The hydantoin derivative for complexing the silver has, at position 5 of the heterocyclic ring, two substituents independently selected from hydrogen, an alkyl group having 1 to 5 carbon atoms and substituted and unsubstituted aryl groups. Optionally, the electrolyte composition may comprise a wetting agent, for example a naphthalenesulfonic acid-formaldehyde polycondensate and/or a sulfopropylated polyalkoxylated naphthol. Furthermore, an alkali metal bromide, preferably potassium bromide, and/or a thiosulfate, preferably an alkali metal thiosulfate such as, e.g. sodium thiosulfate, may optionally be added to the electrolyte. Both alkali metal bromide and thiosulfate serve as matting agents. The alkali metal bromide also produces more uniform deposition results with respect to color. The electrolyte compositions have a pH of 8 to 14. Indeed, without addition of alkali metal bromide or thiosulfate, glossy silver layers appear to be deposited, with no statements made regarding the degree of gloss. Electrolyte compositions with alkali metal bromide and/or thiosulfate provide matte silver coatings. WO 2008/043528 A2 does not make any statements regarding the color of the silver layers.

US 2011/0062030 A1 describes an electrolyte composition for the deposition of metals, particularly silver, on solar cells. The silver is used, for example, in the form of its methanesulfonate. Imidosuccinate derivatives serve as complexing agents for the metal ions. Optionally, a hydantoin derivative may be used as second complexing agent. The composition advantageously contains an additive for increasing the conductivity, preferably a citrate, and a wetting agent, preferably with a polyalkylene oxide chain. The pH of the electrolyte composition is between 8 and 12. Apart from metals to be deposited, which may be present in the form of their methanesulfonates, the composition preferably contains neither further sulfonic acid derivatives nor cyanides. No statements are made regarding the color and gloss of the deposited layers.

US 2012/0067733 A1 describes a method for the deposition of a silver layer on a nickel layer from a cyanide-free electrolytic bath. Suitable silver sources for the bath are silver oxide, silver nitrate, silver sodium thiosulfate, silver gluconate, silver-amino acid complexes such as, e.g. silver-cysteine complexes, silver alkyl sulfonates, e.g. silver methanesulfonate, silver hydantoin compounds and silver-succinimide complexes. The bath contains at least one imide, for example a succinimide, maleimide, phthalimide or a hydantoin derivative. The silver sources are present in comparatively low concentrations of 0.1 to 5 g/l silver, while the imide is used in a concentration of 40 g/l to 120 g/l. Optionally, the bath contains amidosulfonic acid or an alkylsulfonic acid. Furthermore, the bath may optionally contain surface-active substances, wherein these may be anionic, cationic or amphoteric. The electrolytic bath has a pH of 8 to 12 and gives mirror-shiny silver layers on nickel.

US 2012/0067735 A1 describes a cyanide-free electrolyte for the deposition of silver, in which silver is complexed with at least one complexing agent selected from hydantoin, hydantoin derivatives, succinimide and succinimide derivatives. Suitable silver sources for the bath are for example silver oxide, silver nitrate, silver sodium thiosulfate, silver gluconate, silver-amino acid complexes such as, e.g. silver-cysteine complexes, silver alkyl sulfonates, e.g. silver methanesulfonate, silver hydantoin compounds and silver-succinimide complexes. The bath further contains at least one pyridylacrylic acid and at least one organic sulfide selected from dialkyl sulfides and dialkyl disulfides. The combination of pyridylacrylic acids and organic sulfides gives mirror-shiny silver deposits, and the deposition can also take place at high current intensities and high bath temperatures. The electrolyte may additionally contain conducting salts and buffer substances. Its pH is between 8 and 14. With the electrolytes according to US 2012/0067735 A1, mirror-shiny silver layers can be galvanically deposited. This disclosure, however, does not make any statements regarding the color of the deposited layers.

WO 2015/018654 A1 discloses a cyanide-free, acidic and aqueous electrolyte for the deposition of predominantly silver-containing silver-palladium alloys and a method for deposition of these layers. In addition to silver and palladium compounds, the electrolyte contains a tellurium or selenium compound, urea or an amino acid and a sulfonic acid. In this case, the amount of tellurium or selenium influences the silver concentration in the deposited alloy. The urea or the amino acid complex the palladium and increase the stability of the electrolyte. The electrolyte ensures uniform deposition of a corresponding silver-palladium alloy over a wide current density range, which is particularly advantageous for the industrial production of contact materials. The method for the deposition of the silver-palladium alloys is advantageously carried out in the strongly acidic pH range.

US 2016/0122890 A1 discloses a cyanide-free electrolyte for the deposition of silver or silver alloys and a method for the deposition of such layers. The electrolyte according to the invention comprises at least one silver ion source, a sulfonic acid and/or a sulfonic acid derivative, a wetting agent and a hydantoin. The silver coatings or silver alloy coatings that can be deposited from this electrolyte are matte and ductile.

WO 2017/067985 A1 describes an electrolyte containing suitable reducing agents for adjusting the composition of silver-palladium layers. The reducing agents also contribute to improving the layer appearance and to increasing the lightness (L value, CIE Lab) of the deposited layers. WO 2017/067985 A1 also discloses a method for the electrolytic deposition of silver-rich silver-palladium alloys. In addition to silver and palladium compounds, the electrolyte contains a tellurium and/or selenium compound, urea or an amino acid and also a sulfonic acid and furthermore a reducing agent. Here, the amount of tellurium and/or selenium influences the silver concentration in the deposited alloy. The urea or the amino acid complex the palladium. As the reducing agent content increases, the palladium content in the deposited layer increases, and so the reducing agent serves to adjust the layer composition. The also disclosed method for the deposition of silver-palladium alloys is advantageously carried out in the strongly acidic pH range. Due to the palladium, the deposited silver-palladium alloys are darker than pure silver layers.

JP 2018-009227 A discloses a method for the deposition of palladium-silver alloy layers, wherein the weight ratio of Pd to Ag in the layers can range from 1:9 to 9:1. The deposited layers are readily solderable and are suitable as electrical contact materials. The electrolytes for the deposition of the Pd—Ag alloy layers also contain, in addition to palladium salts and silver salts, at least one diamine compound and one heterocyclic compound. The diamine compounds are advantageously alkylated diamines, preferably ethylenediamine and 1,3-propanediamine. The heterocyclic compound is hydantoin or a derivative thereof. 1-(Hydroxymethyl)-5,5-dimethylhydantoin and 5,5-dimethylhydantoin are particularly advantageous. The pH of the electrolyte is between 7.0 and 14.0, most preferably between 10.0 and 11.0. Optionally, the electrolyte may contain conducting salts, buffers, brighteners and wetting agents. No statements are made regarding the color and gloss of the deposited layers. However, it can be assumed, because of the palladium content of at least 10% by weight, that the deposited layers are darker than pure silver layers.

DESCRIPTION OF THE DRAWINGS

This invention is further understood by reference to the drawings wherein.

Figure 1:
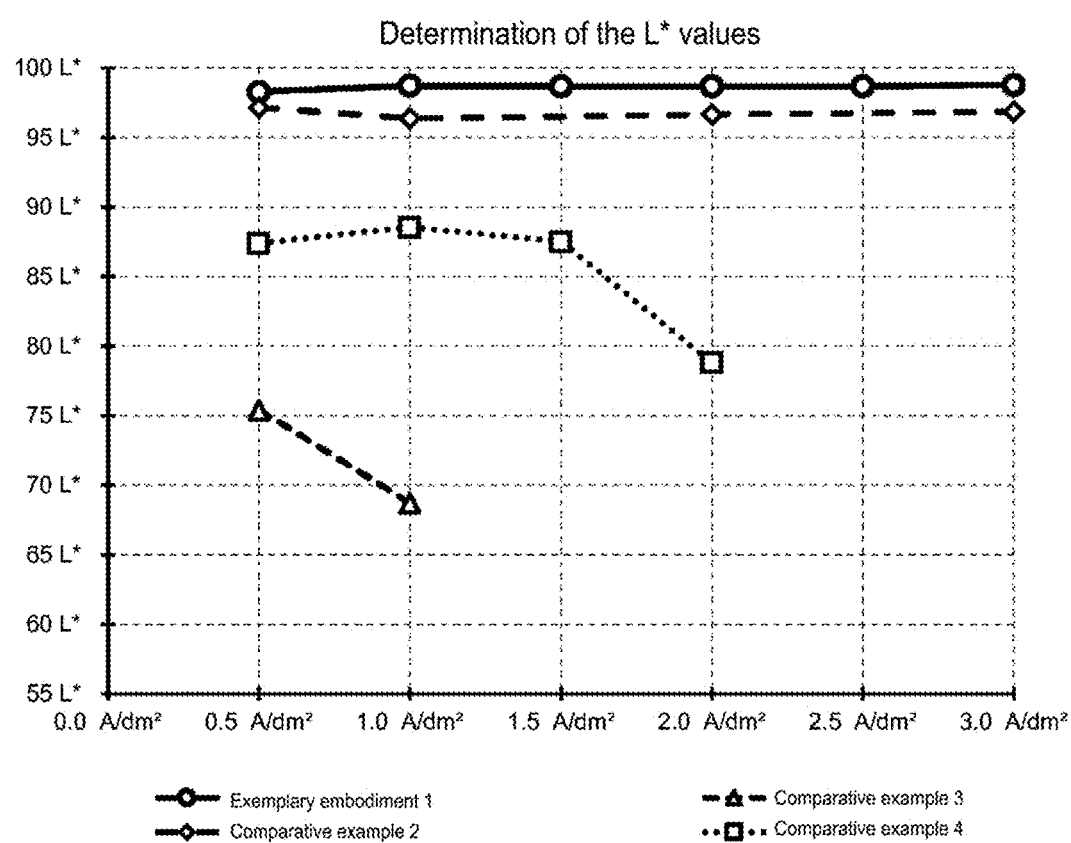
FIG. 1 shows the results of determining the L* values of deposited layers.

In spite of the numerous, already known electrolytes for the electrolytic deposition of silver and silver alloys, there is a further need to offer electrolytes which are superior to the electrolytes of the prior art in terms of the degree of whiteness and gloss of the deposits, bath stability and throughput behavior (metal turnover). For industrial use, such electrolytes should have sufficient stability and make it possible to be able to deposit stable alloy compositions over as wide a current density range as possible. The electrolytes should remain fully functional even after a high current density load, and the deposits produced with these electrolytes should be homogeneous and advantageous in terms of use in technical and decorative applications.

The above objects are achieved by means of an electrolyte having the features of the present claim 1. Subclaims dependent on claim 1 relate to preferred embodiments of an electrolyte according to the invention. Claims 9-13 relate to a method for electrolytic deposition in which an electrolyte according to the invention is used.

By providing an aqueous, cyanide-free electrolyte for the electrolytic deposition of silver and silver alloy coatings, which has the following constituents in dissolved form:
a) at least one silver compound in a concentration of 0.1-150 g/l silver,
b) at least one compound of an alloy metal in a concentration of 0 to 100 g/l alloy metal,
c) at least one compound of formula (I)

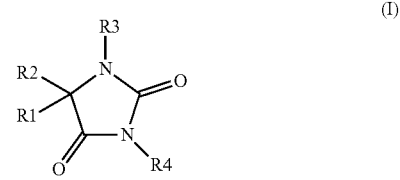

wherein
R1, R2, R3 and R4 independently represent hydrogen, a linear or branched alkyl group having 1 to 5 carbon atoms, an alkoxy group having 1 to 5 carbon atoms, a hydroxyalkyl group having 1 to 5 carbon atoms or an aryl group,
and
wherein the at least one compound of formula (I) is present in a concentration of 1 to 350 g/l,
d) at least one brightener carrier selected from i. at least one amino acid in a concentration of 0.0001-5 mol/l, in particular 0.01-5 mol/l, and/or ii. at least one pyridinecarboxylic acid in a concentration of 0.01-5 mol/l e) at least one brightening agent selected from sulfonamide, 2,2'-sulfanediyldiethanol, cysteine, methionine, aliphatic and aromatic heterocyclic compounds having 5 to 7 ring atoms, wherein the ring of the aliphatic and aromatic heterocyclic compounds contains at least one heteroatom selected from nitrogen and sulfur, and wherein the aliphatic and aromatic heterocyclic compounds optionally contain one or more further heteroatoms selected from nitrogen, oxygen and sulfur, and also mixtures of these brightening agents, wherein the concentration of the brightening agent or of the mixture of brightening agents is 0.005-25 g/l, wherein, if the at least one brightening agent is selected from cysteine and/or methionine and at least one amino acid according to d)i. is selected as brightener carrier, the brightener carrier amino acid is neither cysteine nor methionine, f) an alkali metal hydroxide selected from lithium hydroxide, sodium hydroxide, potassium hydroxide and mixtures thereof in a concentration of 1-200 g/l, g) wherein the electrolyte has a pH of greater than or equal to 7, the stated object is achieved.

Surprisingly, it has been found that with the electrolyte described here, brilliant, glossy and white silver coatings and silver alloy coatings can be deposited on electrically conductive substrates over a wide current density range. Furthermore, the electrolyte according to the invention has high bath stability and high deposition rates and deposition speeds, which makes it particularly advantageous in industrial application. With the present electrolytes, high-quality electrical contact materials can be advantageously produced even in rack and high-speed coating systems. The electrolyte preferably contains only the above constituents.

The electrolyte according to the invention can be used in a current density range of 0.1 to 100 A/dm$^2$. A current density range of 0.5 to 20 A/dm$^2$ is preferred.

It is known to the person skilled in the art that the color and brightness of metallic coatings can be determined with the aid of the so-called L*a*b* measurement according to CIEL*a*b (www.cielab.de), wherein the L* value indicates brightness. The lightness values (L* values) of the silver layers according to the invention are between 95 and 99 L*a*b* (measuring instrument Konica Minolta CM-700, illuminant D65/10). The a* values are between −0.5 and +0.5, the b* values are between 1.5 and 5.0.

Gloss can be assessed by measuring reflection. The silver layers according to the invention have values in the range from 91 to 93.5. The reflection was measured with the BYK-Gardner—Micro-TRI-gloss meter. Measurement was carried out at a 20° angle of incidence and a 20° angle of reflection of the light beam according to EN ISO 7668 (most recent version on date of application). Measurement of the gloss of surfaces is known to the person skilled in the art and information in this regard may be found in, for example, Schriftenreihe Galvanotechnik und Oberflächenbehandlung. Prüfung von funktionellen metallischen Schichten [Publication series: Electroplating and surface treatment: Inspecting functional metal coatings], Section 4.3: Glanz-und Reflexionsmessung an Oberflächen' [Gloss and reflection measurement of surfaces], Eugen G Leuze-Verlag, Saulgau, 1st ed. 1997, pp. 117-125.

Galvanic baths are solutions containing metal salts from which electrochemically metallic precipitates (coatings) can be deposited on substrates (objects). Galvanic baths of this kind are often also termed 'electrolytes'. Accordingly, the cyanide-free and aqueous galvanic baths according to the invention are hereinafter referred to as 'electrolytes'.

The electrolyte according to the invention for the electrolytic deposition of silver coatings and silver alloy coatings, and also the method for the deposition of such silver coatings and silver alloy coatings are explained below, wherein the invention comprises all embodiments listed below either individually or in combination with each other.

The present electrolyte is a cyanide-free, aqueous electrolyte. It is expedient here if all substances present in the electrolyte are as completely dissolved as possible, in order to avoid contamination of the layer with undissolved material during the deposition. In the context of the present invention, a substance is considered to be water-soluble when at least 0.1 g of this substance dissolves in a liter of water at 25° C. Such substances are also referred to hereinafter as "soluble compounds" or "soluble substances".

The silver compound contained in the electrolyte according to the invention is preferably a silver salt which is soluble in this electrolyte. Here, the silver salts are preferably selected from the group consisting of silver methanesulfonate, silver carbonate, silver phosphate, silver pyrophosphate, silver nitrate, silver oxide, silver lactate, silver fluoride, silver bromide, silver chloride, silver iodide and silver sulfate. Silver nitrate, silver carbonate, silver methanesulfonate, silver chloride and silver oxide are particularly preferably used in the electrolyte according to the invention.

Here the person skilled in the art should be guided by the principle that as few additional substances as possible should be added to the electrolyte. For this reason, the person skilled in the art will give the utmost preference to selecting silver methanesulfonate, silver carbonate or silver oxide as the silver salt to be added. It is also possible to use compounds of silver and the further electrolyte constituents (e.g. silver hydantoinate). As regards the concentration of the silver compound employed, the person skilled in the art should be guided by the limit values given above. The silver compound is preferably present in the electrolyte in a concentration of 0.1-150 g/l of silver, more preferably 2-100 g/l of silver and most preferably between 4-40 g/l of silver.

The alloy metals are tin, palladium, antimony, cobalt, indium, iron, nickel, ruthenium, rhodium, platinum, copper, zinc, selenium, tellurium, bismuth, iridium, germanium, gallium, gold, rhenium, tungsten, molybdenum, dysprosium and cerium. They are added to the bath according to the invention in the form of soluble compounds of $Sn^{2+}$, $Sn^{4+}$, $Pd^{2+}$, $Sb^{3+}$, $Co^{2+}$, $In^{3+}$, $Fe^{2+}$, $Fe^{3+}$, $Ni^{2+}$, $Ru^{3+}$, $Ru^{4+}$, $Rh^{3+}$, $Pt^{2+}$, $Pt^{4+}$, $Cu^{2+}$, $Cu^+$, $Zn^{2+}$, $Se^{2+}$ and $Se^{4+}$, $Te^{2+}$, $Bi^{3+}$, $Ir^{3+}$, $Ir^{4+}$, $Ge^{2+}$, $Ge^{4+}$, $Ga^{3+}$, $Au^{3+}$, $Re^{3+}$, $Re^{4+}$, $W^{6+}$, $Dy^{3+}$ and $Ce^{3+}$.

Suitable soluble compounds of the alloy metals mentioned are known to the person skilled in the art and can be used without departing from the scope of protection of the patent claims. Soluble compounds of the alloy metals to be used advantageously are mentioned below, the invention also comprising soluble compounds of these metals which are not explicitly listed.

The divalent tin compound is selected from tin(II) fluoride, tin(II) chloride, tin(II) bromide, tin(II) iodide, tin(II) hydroxide, tin(II) oxide, tin(II) pyrophosphate, tin(II) sulfate, tin(II) methanesulfonate. The divalent tin compound is advantageously selected from tin(II) pyrophosphate, tin(II) sulfate and tin(II) methanesulfonate.

The tetravalent tin compound is selected from sodium hexahydroxostannate(IV), potassium hexahydroxostannate (IV) and mixtures thereof.

The divalent palladium compound is selected from tetraaminepalladium(II) chloride, tetraaminepalladium(II) bromide, palladium hydroxide, palladium chloride, palladium sulfate, palladium pyrophosphate, palladium methanesulfonate, palladium nitrate, palladium phosphate, palladium bromide, diaminedinitritopalladium(II) chloride, diamminedinitritopalladium(II) bromide, diaminedinitritopalladium(II) sulfate, palladium glycinate, potassium dioxalatopalladate, palladium iodide, palladium(II) cyanide, palladium(II) pentacyanonitrosylferrate(III), tetraaminepalladium(II) sulfate, bis(ethylenediamino)palladium(II) carbonate, bis(ethylenediamino)palladium(II) sulfate, bis(ethylenediamino)palladium(II) bromide, bis(acetylacetonato) palladium(II), diaminedichloropalladium(II), palladium oxide hydrate, tetraaminepalladium(II) hydrogencarbonate, bis(ethylenediamino)palladium(II) chloride, palladium acetate, dipotassium cyanopalladate.

The trivalent antimony compound is selected from antimony(III) oxide, antimony(III) fluoride, antimony(III) chloride, antimony(III) bromide, potassium antimony oxide tartrate. The trivalent antimony compound is advantageously selected from antimony(III) oxide and potassium antimony oxide tartrate.

The divalent cobalt compound is selected from cobalt(II) chloride, cobalt(II) oxide, cobalt(II) nitrate, cobalt(II) sulfate, cobalt(II) thiocyanate, cobalt(II) acetate.

The trivalent indium compound is selected from indium (III) chloride, indium(III) gluconate, indium(III) sulfate, and indium(III) oxide. The trivalent indium compound is advantageously selected from indium(III) sulfate, indium(III) chloride and indium(III) gluconate.

The divalent iron compound is selected from iron(II) sulfate hydrate, iron(II) chloride, iron(II) citrate, iron(II) methanesulfonate, ammonium iron(II) citrate, iron(II) chloride hexahydrate, iron(II) pyrophosphate, ammonium iron (II) oxalate, iron(II) phosphonic acid complexes, iron(II) fluoride, iron(II) bromide, iron(II) nitrate, iron(II) thiocyanate, iron(II) hydroxide.

The trivalent iron compound is selected from iron(III) sulfate hydrate $Fe_2(SO_4)_3$, $FeCl_3$, Fe(III) citrate, Fe(III) methanesulfonate, ammonium iron(III) citrate, Fe(III) chloride hexahydrate, Fe(III) pyrophosphate, ammonium iron (III) oxalate, Fe(III) phosphonic acid complexes, Fe(III) fluoride, iron(III) bromide, Fe(III) nitrate, Fe(III) thiocyanate, Fe(III) hydroxide.

The nickel compounds are selected from nickel(II) sulfate heptahydrate, nickel(II) chloride hexahydrate, nickel(II) sulfamate, nickel(II) nitrate hexahydrate and nickel(II) ethylenediamine complex.

The ruthenium compounds are selected from ruthenium (III) fluoride, ruthenium(III) chloride, ruthenium(III) bromide, ruthenium(III) iodide, ruthenium(III) nitrosyl nitrate, ruthenium(III) acetate, ruthenium isonitrile complexes, Ru nitrido-halo complexes of the general formula $[Ru_2N(H_2O)_2X_8]^{3-}$, wherein X is a halide ion, selected from fluoride, bromide, chloride and iodide, for example $[Ru_2N(H_2O)_2Cl_8]^{3-}$, ruthenium nitrido-hydroxo complexes and Ru nitrido-oxalato complexes.

The trivalent rhodium compounds are selected from rhodium(III) fluoride, rhodium(III) chloride, rhodium(III) bromide, rhodium(III) iodide, rhodium(III) oxide hydrate, rhodium(III) methanesulfonate and rhodium(III) sulfate.

The divalent platinum compound is selected from platinum(II) chloride, tetrachloroplatinic(II) acid $H_2(PtCl_4)$, platinum(II) bromide, dinitrosulfatoplatinic(II) acid and salts thereof, diaminodinitritoplatinum(II), tetraamine platinum(II) salts, platinum(II) nitrate and platinum(II) iodide.

The tetravalent platinum compound is selected from hexachloroplatinic(IV) acid $H_2(PtCl_6)$, platinum(IV) fluoride, hexahydroxoplatinic(IV) acid and salts thereof and platinum (IV) bromide.

The divalent copper compound is selected from copper(II) sulfate, copper(II) fluoride, copper(II) chloride, copper(II) bromide, copper(II) iodide, copper(II) hydroxide, copper(II) oxide, copper(II) oxalate, copper(II) carbonate, copper(II) nitrate, copper(II) phosphate, copper(II) pyrophosphate, copper(II) methanesulfonate, copper(II) citrate, copper(II) acetate. The divalent copper compound is advantageously selected from copper(II) sulfate, copper(II) chloride and copper(II) pyrophosphate.

The divalent zinc compound is selected from zinc fluoride, zinc chloride, zinc bromide, zinc iodide, zinc sulfate, zinc oxide, zinc hydroxide, zinc pyrophosphate, zinc citrate, zinc methanesulfonate. The divalent zinc compound is advantageously selected from zinc pyrophosphate, zinc sulfate and zinc methanesulfonate.

Suitable selenium and tellurium compounds are those in which selenium or tellurium is present in oxidation states +4 or +6. Selenium and tellurium compounds are advantageously used in the electrolyte in which selenium or tellurium in oxidation state +4 is present. The selenium and tellurium compounds are particularly preferably selected from tellurites, selenites, tellurous acid, selenious acid, telluric acid, selenium acid, selenocyanates, tellurocyanates and selenate and tellurate. The use of tellurium compounds rather than selenium compounds is generally preferred here. More particularly preferable is the addition of tellurium to the electrolyte in the form of a salt of the tellurous acid in, for example, the form of potassium tellurite.

The trivalent bismuth compound is selected from bismuth (III) hydroxide, bismuth(III) hydroxide, bismuth(III) chloride, bismuth(III) citrate, bismuth(III) bromide, bismuth(III) iodide, bismuth(III) methanesulfonate. The trivalent bismuth compound is advantageously selected from bismuth (III) citrate and bismuth(III) methanesulfonate.

The trivalent iridium compounds are selected from iridium(III) sulfate, iridium(III) chloride, iridium(III/IV) chloride, iridium(IV) chloride, potassium hexabromoiridate(IV), potassium hexachloroiridate(IV), sodium hexabromoiridate (IV), sodium hexachloroiridate(IV), hexachloroiridium(IV) acid, ammonium hexachloroiridate(IV), ammonium hexabromoiridate(IV).

The germanium compounds are selected from the germanium(II) or germanium(IV) halides, germanium(II) selenide, germanium(II) telluride and germanium(IV) oxide.

The gallium compounds are selected from gallium(III) fluoride, gallium(III) chloride, gallium(III) bromide, gallium (III) iodide and gallium(III) oxide.

The gold compounds are selected from alkali metal gold (I) sulfite, ammonium gold(I) sulfite, tetrachlorogold(III) acid, gold as gold(I) hydantoin complex or gold(III) hydantoin complex, potassium dicyanoaurate(I), potassium tetracyanoaurate(III), gold(I) cysteine complex and gold(III) sulfate.

The rhenium compounds are selected from rhenium(III) chloride and rhenium(IV) oxide.

The tungsten compounds are selected from alkali metal tungstate, ammonium tungstate and tungsten oxide; the tungsten(VI) compounds are preferred.

The molybdenum compounds are selected from alkali metal molybdate, ammonium molybdate and molybdenum oxide; the molybdenum(VI) compounds are preferred.

The dysprosium compounds are selected from dysprosium(III) chloride and dysprosium(III) nitrite.

The cerium compounds are selected from cerium(III) chloride and cerium(III) sulfate hydrate.

The at least one compound of an alloy metal is present in the electrolyte in a concentration of 0 to 100 g/l. In a preferred embodiment, the concentration of the at least one alloy metal in the electrolyte is 0 g/l. In this case, aside from silver there is no metal to be deposited present, and the electrolyte serves for the deposition of pure silver coatings. In a further, more preferred, embodiment, the at least one compound of the alloy metal is present in the electrolyte in a concentration of greater than 0 to at most 100 g/l. In this case, as well as silver there is at least one further metal to be deposited present, and the electrolyte serves for the deposition of silver alloy coatings. Advantageously, the concentration of the at least one alloy metal in the electrolyte is 0.05-100 g/l, preferably 0.5-20 g/l, particularly preferably 1-10 g/l.

In the context of the present invention, "at least one compound of an alloy metal" comprises the following variants:
a) a single compound of a single alloy metal is used.
b) several compounds of a single alloy metal are used, i.e. the cations of these compounds originate in all cases from the same alloy metal, while the anions differ. The cations may be present in different oxidation states.
c) compounds of several alloy metals are used, all compounds having the same anion, but the cations differing.
d) several compounds of several alloy metals are used, i.e. both several different anions and several different cations are present.

In cases a) and b), an electrolyte for the deposition of binary silver alloys is obtained, in cases c) and d) an electrolyte for the deposition of at least ternary silver alloys is obtained.

In the present electrolyte, silver is complexed with at least one compound of formula (I):

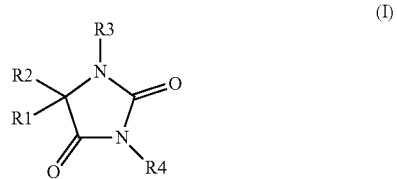

(I)

R1, R2, R3 and R4 independently represent hydrogen, a linear or branched alkyl group having 1 to 5 carbon atoms, an alkoxy group having 1 to 5 carbon atoms, a hydroxyalkyl group having 1 to 5 carbon atoms or an aryl group, The linear or branched alkyl group having 1 to 5 carbon atoms is selected from methyl, ethyl, n-propyl, isopropyl, n-butyl, isobutyl, 2-methylpropyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl.

The alkoxy group having 1 to 5 carbon atoms is selected from methoxy, ethoxy, n-propoxy, isopropoxy, n-butoxy, isobutoxy, 2-methylpropoxy, tert-butoxy, n-pentoxy, 2-pentoxy, 3-pentoxy, 2-methylbutoxy, 3-methylbutoxy, 3-methylbut-2-oxy, 2 methylbut-2-oxy, 2,2-dimethylpropoxy.

The hydroxyalkyl group having 1 to 5 carbon atoms is derived from the alkyl groups mentioned, wherein a hydrogen atom of the particular alkyl group is replaced by a hydroxy group.

The aryl group is selected from phenol, naphthol, benzene, toluene, xylene, cumene.

The compounds of formula (I) are hydantoin and derivatives thereof.

Advantageously, the at least one compound of formula (I) is selected from 1-methylhydantoin, 1,3-dimethylhydantoin, 5,5-dimethylhydantoin, 1-hydroxymethyl-5,5-dimethylhydantoin, 5,5'-diethylhydantoin and 5,5-diphenylhydantoin and mixtures thereof. The at least one compound of formula (I) is particularly preferably 5,5-dimethylhydantoin.

The complex of silver and the at least one compound according to formula (I) is formed in situ from the silver compound used and the at least one compound according to formula (I). The at least one compound according to formula (I) is used in a concentration of 1-350 g/l, preferably 5-200 g/l, particularly preferably 10-100 g/l. In a preferred embodiment of the present invention, silver is employed as a complex of formula (I).

In the electrolyte according to the invention, the molar ratio of the silver to the compound according to formula (I) is 1:2 to 1:6. This applies irrespective of whether a complex of silver and a compound of formula (I) is used as the silver compound or whether another silver compound is used which is not a complex of silver with a compound of formula (I): Overall, the quantity of the compound according to formula (I) in the electrolyte according to the invention is twice to five times as high as the quantity of the silver, irrespective of the proportion of the compound of formula (I) present as silver complex.

The electrolyte according to the invention further contains at least one brightener carrier selected from at least one amino acid in a concentration of 0.0001-5 mol/l, preferably 0.001-1 mol/l and particularly preferably 0.01-0.5 mol/l and/or at least one pyridinecarboxylic acid in a concentration of 0.01-5 mol/l, preferably 0.01-1 mol/l and very preferably 0.1-0.5 mol/l.

The person skilled in the art knows that amino acids are compounds having a carboxyl group and an amino group. These may be essential or non-essential amino acids. Furthermore, these may be alpha, beta or gamma amino acids, it being known to the person skilled in the art that alpha amino acids have at least two, beta amino acids at least three and gamma amino acids at least four carbon atoms. The at least one amino acid may be present in the D form, the L form or as a racemate. If more than one amino acid is used, each individual amino acid may be present, independently of the other amino acids, in the D form, the L form or as a racemate. Advantageously, the at least one amino acid is selected from alanine, arginine, asparagine, aspartic acid, cystine, cysteine, glutamine, glutamic acid, glycine, histidine, isoleucine, leucine, lysine, methionine, phenylalanine, proline, serine, threonine, tryptophan, tyrosine, valine, sarcosine and mixtures thereof. With regard to sulfur-containing amino acids, such as e.g. cysteine or the dimer cystine, it may be advantageous for these to be used only in concentrations of 0.0001-1 mol/l, preferably 0.0005-0.5 mol/l and particularly preferably 0.001-0.01 mol/l in the electrolyte.

In a particularly advantageous embodiment, the at least one amino acid is selected from glycine, alanine, proline, cysteine and sarcosine and mixtures thereof. Most preferably, the amino acid is selected from glycine and sarcosine.

In an advantageous embodiment, the at least one pyridinecarboxylic acid is selected from picolinic acid, picolinic acid amide, nicotinic acid, nicotinamide, isonicotinic acid, isonicotinamide and mixtures thereof. The at least one pyridinecarboxylic acid is preferably selected from nicotinic acid, nicotinamide, picolinic acid and picolinic acid amide. In the context of the present invention, both the free pyridinecarboxylic acids mentioned and the amides thereof are referred to as "pyridinecarboxylic acids". In a very particularly preferred embodiment, the electrolyte according to the invention contains no pyridinecarboxylic acid, but at least one aminocarboxylic acid as mentioned above as brightener carrier.

The at least one brightening agent is advantageously selected from the group of the sulfonamides. Sulfonamides are a group of chemical substances known to the person skilled in the art, some of which act antibiotically (Beyer Walter, Lehrbuch der organischen Chemie [*Textbook of Organic Chemistry*], S. Hirzel Verlag Stuttgart, 22nd edition, 1991, pp. 496, 497, 575-577, 784, 785). In a preferred embodiment, the sulfonamide has a structural element $R_1$—$SO_2$—$NR_2R_3$, wherein $R_1$, $R_2$ and $R_3$, independently of one another, is hydrogen, $(C_5-C_{10})$ alkyl, $(C_1-C_{10})$ cycloalkyl, $(C_6-C_{10})$ aryl, $(C_5-C_{10})$ heteroaryl, $(C_5-C_{10})$ heterocycloalkyl. $R_2$ and $R_3$ may also form a saturated or a mono- or polyunsaturated ring which may have 4 or 5 further atoms, in particular C atoms or 1 or 2 nitrogen or oxygen atoms. This ring may further be substituted.

In this context, $(C_1-C_{10})$ alkyl are saturated or mono- or polyunsaturated alkyl radicals which may be linear or arbitrarily branched. These are preferably selected from methyl, ethyl, n-propyl, isopropyl, n-butyl, isobutyl, 2-methylpropyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl. The radicals considered here may be substituted by heteroatoms, wherein the heteroatoms are preferably selected from the group consisting of oxygen, nitrogen or sulfur. The heteroatoms can likewise in turn be substituted by further organic radicals. These radicals are particularly preferably selected from hydrogen, methyl, ethyl, n-propyl, isopropyl, n-butyl, isobutyl, 2-methylpropyl, tert-butyl, n-pentyl, 2-pentyl, 3-pentyl, 2-methylbutyl, 3-methylbutyl, 3-methylbut-2-yl, 2-methyl but-2-yl, 2,2-dimethyl propyl.

In this context, $(C_3-C_{10})$ cycloalkyl are cyclic alkyl radicals such as, e.g. cyclopropyl, cyclopentyl or cyclohexyl. These radicals may have double bonds. The radicals considered here may be substituted by heteroatoms, wherein the heteroatoms are preferably selected from the group consisting of oxygen, nitrogen or sulfur. The heteroatoms can likewise in turn be substituted by further organic radicals. These radicals are particularly preferably selected from hydrogen, methyl, ethyl, n-propyl, isopropyl, n-butyl, isobutyl, 2-methylpropyl, tert-butyl, n-pentyl, 2-pentyl, 3-pentyl, 2-methylbutyl, 3-methylbutyl, 3-methylbut-2-yl, 2-methyl but-2-yl, 2,2-dimethylpropyl.

$(C_6-C_{10})$ aryl are aromatic cyclic compounds which can optionally be substituted with further radicals selected from methyl, ethyl, n-propyl, isopropyl, n-butyl, isobutyl, 2-methyl propyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl. Most preferably, these are selected from the group consisting of phenol, naphthol, benzene, toluene, xylene, cumene. The radicals considered here may be substituted by heteroatoms, wherein the heteroatoms are preferably selected from the group consisting of oxygen, nitrogen or sulfur. The heteroatoms can likewise in turn be substituted by further organic radicals. These radicals are particularly preferably selected from hydrogen, methyl, ethyl, n-propyl, isopropyl, n-butyl, isobutyl, 2-methylpropyl, tert-butyl, n-pentyl, 2-pentyl, 3-pentyl, 2-methylbutyl, 3-methylbutyl, 3-methylbut-2-yl, 2-methyl but-2-yl, 2,2-dimethylpropyl.

$(C_5-C_{10})$ herteroaryl or $(C_5-C_{10})$ heterocycloalkyl are derived from the above-mentioned cycloalkyl and aryl radicals, with at least one C atom in the ring being exchanged for a heteroatom. Thus, they are preferably aliphatic or aromatic heterocyclic compounds having 5 to 10 ring atoms, wherein the ring of the aliphatic and aromatic heterocyclic compounds contains at least one heteroatom selected from nitrogen and sulfur, and wherein the aliphatic and aromatic heterocyclic compounds optionally contain one or more further heteroatoms selected from nitrogen, oxygen and sulfur. These ring systems can likewise in turn be substituted by further organic radicals. These radicals are particularly preferably selected from methyl, ethyl, n-propyl, isopropyl, n-butyl, isobutyl, 2-methylpropyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl. The $(C_5-C_{10})$ heteroaryl or $(C_5-C_{10})$ heterocycloalkyl radicals may be substituted with heteroatoms, wherein the heteroatoms are preferably selected from the group consisting of oxygen, nitrogen or sulfur. The heteroatoms can likewise in turn be substituted by further organic radicals. These radicals are particularly preferably selected from hydrogen, methyl, ethyl, n-propyl, isopropyl, n-butyl, isobutyl, 2-methylpropyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl.

In a further advantageous embodiment, the at least one brightening agent is sulfonamides, which, as radicals $R_1$, $R_2$ and $R_3$, have an aromatic, optionally heterocyclic compound having 5 to 10 ring atoms, wherein the ring has at least one nitrogen and/or a sulfur atom. Sulfonamides which as radicals $R_1$, $R_2$ and $R_3$ have aromatic, optionally heterocyclic, compounds, and which, in the context of the present invention, can be used as brightening agents, preferably have 5 to 7 ring atoms. At least one of these ring atoms is a nitrogen or sulfur atom. Optionally, one or more further heteroatoms selected from oxygen, nitrogen and sulfur may also be present. These further heteroatoms can likewise be constituents of the aromatic ring, but they can also be present in side chains and groups bonded to the ring. Suitable aliphatic and aromatic heterocyclic compounds are derivatives of tetrahydrothiophene, thiophene, tetrahydrofuran, furan, pyrrolidine, pyrrole, imidazolidines, pyrazolidines, imidazoles, pyrazoles, oxazolidines, isoxazolidines, oxazoles, isoxazoles, thiazolidines, isothiazolidines, thiazoles, isothiazoles, dioxolanes, dithiolanes, triazoles, furazans, oxadiazoles, thiadiazoles, dithiazoles, tetrazoles, piperidines, pyridines, tetrahydropyrans, pyrans, thianes, thiopyrans, piperazines, pyrimidines, diazines, morpholines, oxazines, thiomorpholines, thiazines, dioxanes, dioxins, dithianes, dithiins, hexahydro-1,3,5-triazines, triazines, trioxanes, trithianes, tetrazines, pentazines, azepanes, azepines, oxepanes, oxepines, thiepanes, thiepines, diazepanes, diazepines, thiazepines. Aniline and pyrimidine, pyridine and pyrazine are particularly preferred in this context. The person skilled in the art knows that organic compounds are those based on carbon. For the purposes of the present invention, organic hetero compounds are compounds which contain, in addition to carbon and hydrogen, at least one further atom. This further atom is the "heteroatom".

Advantageously, this is nitrogen, oxygen or sulfur. The aliphatic and aromatic heterocyclic compounds mentioned can bear functional groups. These functional groups are advantageously thio, thiol, carbonyl, carboxyl, alkyl, hydroxyl, sulfonyl and sulfonyl alkyl groups.

In a likewise particularly advantageous embodiment, the at least one brightening agent is selected from sulfonamides substituted with a ($C_6$-$C_{10}$) aryl radical, which bears an amino group preferably in the para position on the aryl radical, e.g. sulfanilamides (https://de.wikipedia.org/wiki/Sulfanilamid) selected from the group consisting of 4-aminobenzene-sulfonamide, 4-amino-N-pyridine-2-yl-benzenesulfonamide, 4-amino-N-(2-pyrimidinyl)benzenesulfonamide, 4-amino-N-(6-chloropyrazin-2-yl)benzenesulfonamide, 4-amino-N-(6-chloro-3-pyridazinyl)benzenesulfonamide, 4-amino-N-(5-methoxy-2-pyrimidinyl)benzenesulfonamide, 4-amino-N-(1,3-thiazol-2-yl)benzenesulfonamide, 4-amino-N-(5-methyl-1,3,4-thiadiazol-2-yl)benzenesulfonamide, 4-amino-N-(4-methyl-1,3-thiazol-2-yl)benzenesulfonamide, 4-amino-N-(4-methoxy-1,2,5-thiadiazol-3-yl)benzenesulfonamide, 4-amino-N-(5-methyl-3-isoxazolyl)benzenesulfonamide, 4-amino-N-(4-methyl-2-pyrinidinyl)benzenesulfonamide, 4-amino-N-(5-methylpyrimidinyl)benzenesulfonamide, 4-amino-N-(6-methoxypyridazine-3-yl)benzenesulfonamide, 4-amino-N-(3-methoxy-2-pyrazinyl)benzenesulfonamide, 4-amino-N-(4,5-dimethyl-1,3-oxazol-2-yl)benzenesulfonamide, 4-amino-N-(3,4-dimethyl-5-isoaxazolyl)benzenesulfonamide, N-(3,3-dimethylacroyl)sulfanilamide, 4-amino-N-(4,6-dimethyl-2-pyrimidinyl)benzenesulfonamide, 4-amino-N-(2,6-dimethyl-2-pyrimidine-4-yl)benzenesulfonamide, 4-amino-N-(6-methoxy-2-methylpyrimidine-4-yl)benzenesulfonamide, 4-amino-N-(2,6-dimethoxy-4-pyrimidinyl)benzenesulfonamide, 4-amino-N-(5,6-dimethoxy-4-pyrimidinyl)benzenesulfonamide, 4-amino-N-(2-phenylpyrazol-3-yl)benzenesulfonamide, 2-hydroxy-5-((2-((pyridinyl)sulfonyl)phenyl)azo)benzoic acid, 4-aminophenyl-sulfonylthiourea, 1-(4-aminobenzenesulfonyl)urea, 4-(aminomethyl)benzenesulfonamide, N-(p-aminophenyl-sulfonyl)acetamide, 4-amino-N-(diaminomethylene)benzenesulfonamide.

The at least one brightening agent can likewise be selected from the compounds 2,2'-sulfanediyldiethanol, cysteine, methionine, aliphatic and aromatic heterocyclic compounds having 5 to 7 ring atoms, wherein the ring of the aliphatic and aromatic heterocyclic compounds contains at least one heteroatom selected from nitrogen and sulfur, and wherein the aliphatic and aromatic heterocyclic compounds optionally contain one or more further heteroatoms selected from nitrogen, oxygen and sulfur, and also mixtures of these brightening agents.

Aliphatic and aromatic heterocyclic compounds, which can be used in this respect as brightening agents, have 5 to 7 ring atoms. At least one of these ring atoms is a nitrogen or sulfur atom. Optionally, one or more further heteroatoms selected from oxygen, nitrogen and sulfur may also be present. These further heteroatoms can likewise be constituents of the aromatic or aliphatic ring, but they can also be present in side chains and functional groups bonded to the ring.

Suitable aliphatic heterocyclic compounds in this context are derivatives of tetrahydrothiophene, thiophene, tetrahydrofuran, furan, pyrrolidine, pyrrole, imidazolidines, pyrazolidines, imidazoles, pyrazoles, oxazolidines, isoxazolidines, oxazoles, isoxazoles, thiazolidines, isothiazolidines, thiazoles, isothiazoles, dioxolanes, dithiolanes, triazoles, furazans, oxadiazoles, thiadiazoles, dithiazoles, tetrazoles, piperidines, pyridines, tetrahydropyrans, pyrans, thianes, thiopyrans, piperazines, diazines, morpholines, oxazines, thiomorpholines, thiazines, dioxanes, dioxins, dithianes, dithiins, hexahydro-1,3,5-triazines, triazines, trioxanes, trithianes, tetrazines, pentazines, azepanes, azepines, oxepanes, oxepines, thiepanes, thiepines, diazepanes, diazepines, thiazepines.

The aliphatic and aromatic heterocyclic compounds mentioned can bear functional groups. These functional groups are advantageously thio, thiol, carbonyl, carboxyl, alkyl, hydroxyl, sulfonyl and sulfonyl alkyl groups.

In a particularly advantageous embodiment in this regard, the at least one brightening agent is an aliphatic or aromatic heterocyclic compound having 5 to 7 ring atoms, wherein the ring has a nitrogen atom and a sulfur atom.

In an extremely advantageous embodiment in this regard, the at least one brightening agent is selected from cysteine, 2,2'-sulfanediyldiethanol, 2-mercaptonicotinic acid, pyridine-3-sulfonic acid, thiomorpholine, 1,2,3-thiadiazole, 1,2,4-thiadiazole, 1,2,5-thiadiazole and 1,3,4-thiadiazole and derivatives thereof. Particular preference is given to thiomorpholine, also referred to as tetrahydro-2H-1,4-thiazine according to IUPAC nomenclature.

If the at least one brightening agent is selected from cysteine and/or methionine and at least one amino acid is selected as a brightener carrier, the brightener carrying amino acid is neither cysteine nor methionine.

The use of cysteine and/or methionine in the electrolyte according to the invention as a brightener carrier or brightening agent according to the above definition is explained below using several examples:

a) the at least one brightening agent is selected from cysteine and/or methionine Then:
if at least one amino acid is selected as a brightener carrier, this brightener carrier amino acid is not cysteine or methionine.
Optionally, the electrolyte according to the invention may contain at least one pyridinecarboxylic acid.

b) the at least one brightening agent is selected from 2,2'-sulfanediyldiethanol or aliphatic and aromatic heterocyclic compounds according to the above definition.

Then:
If at least one amino acid is selected as brightening agent, it may be essential or non-essential amino acids according to the above definition, including cysteine and/or methionine.
Optionally, the electrolyte according to the invention may contain at least one pyridinecarboxylic acid.

If the at least one brightening agent is selected from cysteine and/or methionine, each of these two amino acids can be present, independently of the other, in the D form, the L form or as racemate.

Furthermore, with the combination of brightener carriers and brightening agents, the following combination is also possible:

c) The at least one brightener carrier is at least one pyridinecarboxylic acid according to the above definition. No amino acid is used as brightener carrier. The brightening agent is selected from 2,2'-sulfanediyldiethanol, cysteine, methionine and aliphatic and aromatic heterocyclic compounds according to the above definition.

The terms "brightener carrier" and "brightening agent" are known to those skilled in the art. Brightener carriers are also referred to as "primary brighteners". In the galvanic deposition of layers from an electrolyte, they bring about a certain gloss, but not a high gloss, and this often occurs only in a limited current density range. Brightener carriers often act to reduce particle size. Brightening agents are also referred to as "secondary brighteners". They bring about a high gloss of the deposited layers, but are likewise often only effective in a limited current density range. High gloss over a wide range of current densities is sometimes possible through the combination of suitable brightener carriers and brightening agents.

The brightening agents or the mixture of brightening agents are present in a concentration in the electrolyte of 0.005-25 g/l, preferably 0.01-5 g/l and particularly preferably 0.05-1 g/l.

The electrolyte according to the invention further contains an alkali metal hydroxide selected from lithium hydroxide, sodium hydroxide, potassium hydroxide and mixtures thereof in a concentration of 1-200 g/l, preferably 5-150 g/l, particularly preferably 10-100 g/l. In an advantageous embodiment, the alkali metal hydroxide is potassium hydroxide. The pH of the electrolyte according to the invention is greater than or equal to 8; advantageously, it is between 9 and 11.

The cyanide-free, aqueous electrolyte according to the invention optionally contains one or more wetting agents.

In a preferred embodiment, the at least one wetting agent is selected from
  nonionic wetting agents such as, e.g. beta-naphthene ethoxylate potassium salt, fatty alcohol polyglycol ethers, polyethyleneimines, polyethylene glycols and mixtures thereof. Wetting agents having a molecular weight below 2000 glmol are particularly advantageous.
  anionic wetting agents such as, e.g. N-dodecanoyl-N-methylglycine, (N-lauroylsarcosine) Na salt, alkyl collagen hydrolysate, 2-ethylhexyl sulfate Na salt, lauryl ether sulfate Na salt and mixtures thereof,
  cationic wetting agents such as, e.g. 1H-imidazoliuml-ethenyl (or 3-methyl)-, methylsulfate homopolymers In the electrolyte according to the invention, typically anionic and nonionic surfactants can be used as wetting agents, such as, e.g. polyethylene glycol adducts, fatty alcohol sulfates, alkyl sulfates, alkyl sulfonates, aryl sulfonates, alkylaryl sulfonates, heteroaryl sulfates, betaines, fluorosurfactants and salts and derivatives thereof (see also: Kanani, N: Galvanotechnik [*Electroplating technology*]; Hanser Verlag, Munich Vienna, 2000; pp. 84 et seq.).

In a further advantageous embodiment, the electrolyte according to the invention contains at least one further salt. The anions of these salts are selected from the group of sulfates, fluorides, chlorides, bromides, iodides, carbonates, formates, acetates, propionates, butyrates, valerates, nitrates, nitrites, sulfonates, alkylsulfonates, in particular methanesulfonates, amidosulfonates, sulfamates, anions of aminocarboxylic acids and N-heterocyclic carboxylic acids. The cations of these salts are selected from ammonium, lithium, sodium and potassium ions. In the case of polyprotonated acids, one or all of the hydrogen atoms may be replaced by the cations mentioned. If more than one hydrogen atom is replaced by one of the cations mentioned, these cations may be identical or different. The at least one further salt is hereinafter also referred to as "conducting salt". The at least one conducting salt is selected from the sodium, potassium and ammonium salts of sulfuric acid, hydrochloric acid, methanesulfonic acid, carbonic acid, nitric acid and phosphoric acid. In an advantageous embodiment, the at least one conducting salt is a potassium salt, particularly preferably potassium methanesulfonate and/or potassium nitrate. In an advantageous embodiment, the at least one conducting salt is used in a concentration of 1 to 200 g/l, preferably 10 to 100 g/l.

The present invention also relates to a method for the electrolytic deposition of silver coatings and silver alloy coatings from an electrolyte according to the invention, wherein an electrically conductive substrate is immersed in the electrolyte and a flow of current is established between an anode in contact with the electrolyte and the substrate as cathode. It should be noted that the embodiments termed as preferable for the electrolyte also apply mutatis mutandis to the method addressed here.

The temperature prevailing during the deposition of the silver coatings and silver alloy coatings can be selected as desired by the person skilled in the art. Their decision is thereby oriented, on the one hand, toward an adequate deposition rate and applicable current density range, and on the other toward economic aspects or the stability of the electrolyte. It is advantageous to set the temperature to 20° C. to 90° C., preferably 40° C. to 80° C., and particularly preferably 50° C. to 70° C.

The current density which is established in the electrolyte according to the invention between the cathode and the anode during the deposition process can be selected by the person skilled in the art according to the efficiency and quality of deposition. Depending on the application and coating plant type, the current density in the electrolyte is advantageously set to 0.1 to 100 A/dm$^2$. If necessary, current densities can be increased or reduced by adjusting the system parameters, such as the design of the coating cell, flow rates, the anode or cathode conditions, and so on. A current density of 0.1-100 A/dm$^2$ is advantageous, 0.2-50.0 A/dm$^2$ is preferable, and 0.5-30 A/dm$^2$ most preferable.

In the context of the present invention, low, medium and high current density ranges are defined as follows:
  Low current density range: 0.1 to 0.75 A/dm$^2$,
  Medium current density range: greater than 0.75 A/dm$^2$ to 5 A/dm$^2$,
  High current density range: greater than 5 A/dm$^2$.

The electrolyte according to the invention and the method according to the invention can be used for the electrolytic deposition of silver coatings and silver alloy coatings for technical applications, for example electrical plug connections and printed circuit boards, and for decorative applications such as jewelry and clocks. In an advantageous embodiment of the present invention, a low current density range is used in the electrolytic deposition of silver coatings and silver alloy coatings, and the at least one brightener carrier contains 0.2-3 mol/l of the at least one amino acid and 0.01-0.5 mol/l of the at least one pyridinecarboxylic acid.

In an advantageous embodiment of the present invention, a medium current density range is used in the electrolytic deposition of silver coatings and silver alloy coatings, and the at least one brightener carrier contains 0.1-1.5 mol/l of the at least one amino acid and 0.1-1 mol/l of the at least one pyridinecarboxylic acid.

In an advantageous embodiment of the present invention, a high current density range is used in the electrolytic deposition of silver coatings and silver alloy coatings, and the at least one brightener carrier contains 0.01-0.1 mol/l of the at least one amino acid and 0.25-2.5 mol/l of the at least one pyridinecarboxylic acid.

As has already been indicated, the electrolyte according to the invention is an alkaline type. The pH should be greater than or equal to 7 and particularly preferably between 8 and 11, better still between 9 and 10.5. It may be that fluctuations with regard to the pH value of the electrolyte occur during electrolysis. In one preferred embodiment of the present method, the person skilled in the art therefore proceeds in monitoring the pH value during electrolysis, and if necessary adjusting it to the nominal value. Potassium hydroxide or methanesulfonic acid is advantageously used to adjust the pH. Alternatively, lithium hydroxide or sodium hydroxide or mixtures of these alkali metal hydroxides can also be used instead of potassium hydroxide.

Various anodes can be employed in the use of the electrolyte. Soluble or insoluble anodes are just as suitable as the combination of soluble and insoluble anodes. If a soluble anode is used, a silver anode is particularly preferred.

Preferably used as insoluble anodes are those made of a material selected from the group consisting of platinized titanium, graphite, mixed metal oxides, glassy carbon anodes, and special carbon material (DLC. "diamond-like carbon"), or combinations of these anodes. Insoluble anodes of platinized titanium or titanium coated with mixed metal oxides are advantageous, the mixed metal oxides being preferably selected from iridium oxide, ruthenium oxide, tantalum oxide, and mixtures thereof. Also advantageously used for the implementation of the invention are iridium-transition metal oxide-mixed oxide anodes, more preferably mixed oxide anodes composed of iridium-ruthenium mixed oxide, iridium-ruthenium-titanium mixed oxide, or iridium-tantalum mixed oxide. More information may be found in Cobley, A. J. et al. (The use of insoluble Anodes in Acid Sulphate Copper Electrodeposition Solutions, Trans IMF, 2001, 79(3), pp. 113 and 114).

Depending on the embodiment, the deposited silver coatings and silver alloy coatings can have a thickness of up to several millimeters, preferably 0.005-500 µm, particularly preferably 0.01-25 µm and very particularly preferably 0.5-10 µm.

Thin layer thicknesses in the range from 0.1 to 0.3 µm silver, for example, are typically used for the coating of plastic caps in rack operation. Here, low current densities in the range from 0.25 to 0.75 $A/dm^2$ are used. A further application of low current densities is used in the drum or vibration technique, for example when coating contact pins. Here, approximately 0.5 to 3 µm of silver are applied in the current density range from 0.25 to 0.75 $A/dm^2$. Layer thicknesses in the range from 1 to 10 µm are typically deposited in rack operation, predominantly for decorative applications, with current densities in the range from 1 to 5 $A/dm^2$. For technical applications, sometimes even up to 25 µm layer thicknesses are deposited. In continuous systems, layer thicknesses are deposited over a relatively wide range of approximately 0.5 to approximately 5 µm with the highest possible deposition rates and thus with the highest possible current densities of between 5 and 30 $A/dm^2$. In addition, there are also special applications in which relatively high layer thicknesses of a few 10 µm up to a few millimeters, for example in the case of electroforming, are deposited.

Pulsed direct current can also be used instead of direct current. The current flow is thereby interrupted for a certain period of time (pulse plating). In reverse pulse plating, the polarity of the electrodes is changed so that a partially anodic stripping of the coating takes place. This way, the layer buildup is controlled in continuous alternation with cathodic pulses. The use of simple pulse conditions such as, e.g. 1 s current flow ($t_{on}$) and 0.5 s pulse pause ($t_{off}$) at medium current densities resulted in homogeneous, glossy and white coatings.

Suitable substrate materials typically used herein are copper-based materials such as pure copper, brass, or bronze, iron-based materials such as iron or stainless steel, nickel, gold and silver. The substrate materials can also be multilayer systems which have been coated galvanically or with another coating technique. This relates, for example, to circuit board base material or iron materials which have been nickel-plated or copper-plated and then optionally gold-plated or coated with pre-silver. Another substrate material is a wax core precoated with silver conductive varnish (electroforming).

A special case of a silver electrolyte for the purposes of this invention is a pre-silver or silver stripping electrolyte. This is intended to mean an electrolyte which typically contains little silver and many complexing agents. As a result, no silver can be deposited by charge exchange, but rather only by applying a voltage. Layers deposited by charge exchange are poorly adhering, therefore a thin layer of pre-silver is often deposited before a thicker silver layer is applied with another electrolyte (see Example 4).

The electrolyte according to the invention has long-term stability and high anode solubility. The method according to the invention for the electrolytic deposition of silver coatings and silver alloy coatings from this electrolyte produces very white coatings, the color of which is close to the white point of the L*a*b* color space. At the white point, L*=100 and a* and b* are equal to zero. Even at high layer thicknesses above 5 µm, the coatings are high-gloss, brilliant and very tarnish resistant, i.e. no subsequent yellowish discoloration occurs. Such coatings could hitherto only be deposited by cyanide-based electrolytes. Silver coatings and silver alloy coatings can be deposited over a very wide current density range with the aid of the electrolyte according to the invention.

EXEMPLARY EMBODIMENTS 1 liter of the electrolyte mentioned below is heated using a magnetic stirrer, with stirring with a 60 mm long cylindrical magnetic stirrer rod at at least 200 rpm to the temperature stated in the exemplary embodiment. This stirring and temperature is also maintained during coating.

After reaching the desired temperature, the pH of the electrolyte is adjusted to the value mentioned in the exemplary embodiment using a KOH solution (c=0.5 g/ml) and methanesulfonic acid (c=70%).

Two plates of fine silver with at least 99.9% purity serve as anodes. These anodes may also be covered with bags made of textiles, filter paper or a semi-permeable membrane such as Nafion.

The cathode used is a mechanically polished brass sheet having at least 0.2 $dm^2$ surface area, which was previously coated with at least 5 µm of nickel from an electrolyte which produces high-gloss layers. An approximately 0.1 µm thick gold layer can also be deposited on the nickel layer.

These cathodes are cleaned before introduction into the electrolyte using electrolytic degreasing (5-7 V) and sulfuric acid-containing pickling (c=5% sulfuric acid). Between each cleaning step and prior to introduction into the electrolyte, the cathode is rinsed with deionized water.

The cathode is positioned in the electrolyte between the anodes and moved parallel thereto at a minimum of 5 cm/second; the distance between anode and cathode must not change during this process.

In the electrolyte, the cathode is coated by applying an electric direct current between anode and cathode. The current intensity is selected in such a way that at least 0.5 $A/dm^2$ is achieved on the surface. Higher current densities can be selected if the electrolyte mentioned in the application example is capable of producing layers which can be used in a technically decorative manner.

The duration of the current flow is selected in such a way that at least one layer thickness of 1.5 μm on average is achieved over the surface. Higher layer thicknesses can be produced if the electrolyte mentioned in the application example is capable of producing these at a quality which can be used in a technically decorative manner.

After coating, the cathode is removed from the electrolyte and rinsed with deionized water. After the coating, a customary treatment can be carried out in hot water, complexing agent solution, pickling or a treatment with tarnish protection, e.g. based on octadecanethiols.

The cathodes can be dried by compressed air, hot air or centrifugation.

The surface area of the cathode, the magnitude and duration of the applied current and the weight of the cathode before and after coating are documented and used to determine the average layer thickness and the efficiency of the deposition.

The color of the deposited layers is determined and documented by an L*a*b* measurement according to CIEL*a*b.

Experiments and comparative experiments according to the invention are given in the tables below.

Potassium hydroxide and methanesulfonic acid, which are used to adjust and set the pH, are not explicitly listed in the tables. The person skilled in the art knows how to adjust or set the pH. In the production of the electrolytes according to the invention, it is possible first to prepare an aqueous solution of all components mentioned in the table and to subsequently adjust the pH to the desired value with potassium hydroxide or methanesulfonic acid. Alternatively, it is also possible first to initially charge a potassium hydroxide solution, then add the hydantoin derivative thereto, and subsequently to add all other ingredients and finally to adjust the pH to the desired value with potassium hydroxide or methanesulfonic acid. During the deposition of the silver layers or silver alloy layers, the pH can also be adjusted with potassium hydroxide or methanesulfonic acid.

TABLE 1

Exemplary embodiments according to the invention

| Component | Concentration | Example no. | | | | | |
|---|---|---|---|---|---|---|---|
| | | 1 | 2 | 3 | 4 | 5 | 6 |
| Silver (as silver methanesulfonate) | g/l | 20 | 20 | 40 | 0 | 10 | 0 |
| Silver (as silver nitrate) | g/l | 0 | 0 | 0 | 45 | 0 | 0 |
| Silver (as silver oxide) | g/l | 0 | 0 | 0 | 0 | 0 | 0 |
| Silver (as silver hydantoin complex) | g/l | 0 | 0 | 0 | 0 | 0 | 10 |
| Tin (as potassium hexahydroxostannate(IV)) | g/l | 0 | 0 | 0 | 0 | 30 | 0 |
| Palladium (as palladium(II) bis(ethylenediamine) sulfate) | g/l | 0 | 0 | 0 | 0 | 0 | 5 |
| Rhodium (as rhodium(III) sulfate) | g/l | 0 | 0 | 0 | 0 | 0 | 0 |
| Potassium nitrate | g/l | 0 | 0 | 0 | 0 | 0 | 0 |
| Potassium chloride | g/l | 0 | 0 | 0 | 0 | 8 | 8 |
| Potassium methanesulfonate | g/l | 0 | 0 | 0 | 0 | 0 | 0 |
| Hydantoin | g/l | 0 | 0 | 0 | 0 | 0 | 0 |
| 5,5'-Dimethylhydantoin | g/l | 150 | 150 | 120 | 160 | 50 | 0 |
| 5,5'-Diethylhydantoin | g/l | 0 | 0 | 0 | 0 | 0 | 50 |
| Glycine | g/l | 40 | 0 | 0.5 | 35 | 0 | 0 |
| 2,2'-Sulfanediyldiethanol | g/l | 0 | 0 | 0 | 0 | 0 | 0 |
| Tetrahydro-2H-1,4-thiazine | ml/l | 0.2 | 0 | 0.2 | 0.4 | 0 | 0 |
| Cysteine | g/l | 0 | 0.2 | 0 | 0 | 0 | 0 |
| Beta-alanine | g/l | 0 | 50 | 0 | 0 | 0 | 0 |
| Methionine | g/l | 0 | 0 | 0 | 0 | 0 | 0 |
| Proline | g/l | 0 | 0 | 0 | 0 | 0 | 0 |
| Sarcosine | g/l | 0 | 0 | 0 | 0 | 0 | 0 |
| L-Glutamic acid | g/l | 0 | 0 | 0 | 0 | 0 | 0 |
| 2-Mercaptonicotinic acid | g/l | 0 | 0 | 0 | 0 | 0 | 0 |
| Picolylamine | ml/l | 0 | 0 | 0 | 0 | 0 | 0 |
| Nicotinic acid | g/l | 0 | 0 | 100 | 0 | 0 | 0 |
| Nicotinamide | g/l | 0 | 0 | 0 | 100 | 0 | 0 |
| Parameters/observations | | | | | | | |
| pH | | 9.6 | 9.6 | 10 | 9 | 12.1 | 9.5 |
| Temperature [° C.] | | 65 | 55 | 65 | 65 | 40 | 40 |
| Current density [A/dm2] | | 0.5-3 | 0.5-1.5 | 5-20 | 0.1-5 | 1 | 2 |
| Movement (observation 1) | | a | a | c | d | a | a |
| Anode (observation 2) | | a | a | b | a | a | a |
| Appearance (observation 3) | | a | a | b | a | b. gray | a, gray |
| Layer thickness [μm] | | 1.5 | 1.6 | 2 | | 2.07 | 1.77 |
| Color [L*a*b*] | | | | | ND | | |
| L* | | 98.7 | 92.2 | 98.5 | | 54.32 | 74.68 |
| a* | | −0.09 | −0.3 | −0.10 | | +2.81 | −0.84 |
| b* | | +1.88 | +4.32 | 1.78 | | +15.07 | −1.37 |
| Silver content [wt %] | | 100 | 100 | 100 | 100 | 96.3 | 92.1 |
| Electrolyte stability (observation 4) | | a | a | a | a | a | a |

TABLE 1-continued

| Component | Concentration | Example no. 7 | 8 | 9 | 10 | 11 | 12 |
|---|---|---|---|---|---|---|---|
| Silver (as silver methanesulfonate) | g/l | 10 | 10 | 5 | 10 | 10 | 10 |
| Silver (as silver nitrate) | g/l | 0 | 0 | 0 | 0 | 0 | 0 |
| Silver (as silver oxide) | g/l | 0 | 0 | 0 | 0 | 0 | 0 |
| Silver (as silver hydantoin complex) | g/l | 0 | 0 | 0 | 0 | 0 | 0 |
| Tin (as potassium hexahydroxostannate(IV)) | g/l | 0 | 0 | 0 | 0 | 0 | 0 |
| Palladium (as palladium(II) bis(ethylediamine) sulfate) | g/l | 0 | 0 | 0 | 0 | 0 | 0 |
| Rhodium (as rhodium(III) sulfate) | g/l | 6 | 0 | 0 | 0 | 0 | 0 |
| Potassium nitrate | g/l | 0 | 0 | 0 | 0 | 0 | 0 |
| Potassium chloride | g/l | 8 | 0 | 0 | 0 | 0 | 0 |
| Potassium methanesulfonate | g/l | 0 | 0 | 30 | 0 | 0 | 0 |
| Hydantoin | g/l | 0 | 0 | 0 | 0 | 0 | 0 |
| 5,5'-Dimethylhydantoin | g/l | 50 | 75 | 150 | 60 | 60 | 75 |
| 5,5'-Diethylhydantoin | g/l | 0 | 0 | 0 | 0 | 0 | 0 |
| Glycine | g/l | 0 | 40 | 100 | 30 | 30 | 20 |
| 2,2'-Sulfanediyldiethanol | g/l | 0 | 0 | 0 | 0 | 0 | 0 |
| Tetrahydro-2H-1,4-thiazine | ml/l | 0 | 0 | 0 | 0 | 0 | 0.2 |
| Cysteine | g/l | 0 | 0.5 | 0 | 0.2 | 0.2 | 0 |
| Beta-alanine | g/l | 0 | 0 | 0 | 0 | 0 | 0 |
| Methionine | g/l | 0 | 0 | 0 | 0 | 0 | 0 |
| Proline | g/l | 0 | 0 | 0 | 0 | 0 | 0 |
| Sarcosine | g/l | 0 | 0 | 0 | 0 | 0 | 0 |
| L-Glutamic acid | g/l | 0 | 0 | 0 | 0 | 0 | 0 |
| Toluenesulfonamide | g/l | 0 | 0 | 0 | 0 | 0 | 0 |
| Mercaptonicotinic acid | g/l | 0 | 0 | 0 | 0 | 0 | 0 |
| Picolylamine | ml/l | 0 | 0.05 | 0 | 0 | 0 | 0 |
| Nicotinic acid | g/l | 0 | 0 | 0 | 30 | 0 | 0 |
| Nicotinamide | g/l | 0 | 0 | 0 | 0 | 40 | 20 |
| Parameters/observations | | | | | | | |
| pH | | 12.8 | 9.5 | 8.8 | 9.5 | 9.5 | 9.5 |
| Temperature [° C.] | | 40 | 55 | 55 | 55 | 55 | 65 |
| Current density [A/dm2] | | 1 | 0.5 | 0.5 | 0.5-1.0 | 0.25-1.0 | 0.5-2.0 |
| Movement (observation 1) | | a | b | a | a | a | a |
| Anode (observation 2) | | a | a | a, b | a | a | a |
| Appearance (observation 3) | | a | a | a | a | a | a |
| Layer thickness [μm] | | 2.39 | 2 | 0.1 | 2 | 2 | 2 |
| Color [L*a*b*] | | | | ND | | | |
| L* | | 80.91 | 97.8 | | 98 | 98.0 | 99.4 |
| a* | | −1.76 | −0.44 | | −0.4 | −0.5 | −0.09 |
| b* | | +4.36 | +4.06 | | +3.7 | +4.0 | +1.4 |
| Silver content [wt %] | | 93.9 | 100 | 100 | 100 | 100 | 100 |
| Electrolyte stability (observation 4) | | a | a | a | a | a | a |

| Component | Concentration | Example no. 13 | 14 | 15 | 16 | 17 | 18 |
|---|---|---|---|---|---|---|---|
| Silver (as silver methanesulfonate) | g/l | 0 | 10 | 10 | 10 | 30 | 30 |
| Silver (as silver nitrate) | g/l | 0 | 0 | 0 | 0 | 0 | 0 |
| Silver (as silver oxide) | g/l | 10 | 0 | 0 | 0 | 0 | 0 |
| Silver (as silver hydantoin complex) | g/l | 0 | 0 | 0 | 0 | 0 | 0 |
| Tin (as potassium hexahydroxostannate(IV)) | g/l | 0 | 0 | 0 | 0 | 0 | 0 |
| Palladium (as palladium(II) bis(ethylediamine) sulfate) | g/l | 0 | 0 | 0 | 0 | 0 | 0 |
| Rhodium (as rhodium(III) sulfate) | g/l | 0 | 0 | 0 | 0 | 0 | 0 |
| Potassium nitrate | g/l | 10 | 0 | 0 | 0 | 0 | 0 |
| Potassium chloride | g/l | 0 | 0 | 0 | 0 | 0 | 0 |
| Potassium methanesulfonate | g/l | 0 | 0 | 0 | 0 | 0 | 0 |
| Hydantoin | g/l | 0 | 0 | 0 | 0 | 0 | 0 |
| 5,5'-Dimethylhydantoin | g/l | 60 | 150 | 75 | 75 | 225 | 150 |
| 5,5'-Diethylhydantoin | g/l | 0 | 0 | 0 | 0 | 0 | 0 |
| Glycine | g/l | 40 | 50 | 20 | 20 | 0 | 40 |
| 2,2'-Sulfanediyldiethanol | g/l | 0 | 0 | 1 | 0 | 0 | 0 |
| Tetrahydro-2H-1,4-thiazine | ml/l | 0 | 0 | 0 | 0.2 | 0.2 | 0 |
| Cysteine | g/l | 0 | 0 | 0 | 0 | 0.2 | 0 |
| Beta-alanine | g/l | 0 | 0 | 0 | 0 | 0 | 0 |

TABLE 1-continued

| Component | | | | | | | |
|---|---|---|---|---|---|---|---|
| Methionine | g/l | 0 | 0 | 0 | 0 | 0.2 | 1 |
| Proline | g/l | 0 | 0 | 0 | 0 | 0 | 0 |
| Sarcosine | g/l | 0 | 0 | 0 | 0 | 0 | 0 |
| L-Glutamic acid | g/l | 0 | 0 | 0 | 0 | 0 | 0 |
| Toluenesulfonamide | g/l | 1.0 | 2.0 | 0 | 0 | | |
| Mercaptonicotinic acid | g/l | 0.1 | 0.2 | 0 | 0 | 0 | 0 |
| Picolylamine | ml/l | 0 | 0 | 0 | 0 | 0 | 0 |
| Nicotinic acid | g/l | 0 | 0 | 0 | 20 | 0 | 0 |
| Nicotinamide | g/l | 0 | 0 | 20 | 0 | 0 | 0 |
| Parameters/observations | | | | | | | |
| pH | | 9.5 | 9.7 | 9.5 | 9.5 | 9.6 | 9.6 |
| Temperature [° C.] | | 50 | 60 | 60 | 60 | 60 | 60 |
| Current density [A/dm2] | | 0.5-1.0 | 0.5-1.5 | 0.5-2.0 | 0.25-1.5 | 0.1-0.7 | 0.1-1 |
| Movement (observation 1) | | a | a | a | a | d | d |
| Anode (observation 2) | | a | a | a | a | a | a |
| Appearance (observation 3) | | a | a | a | a | a | a |
| Layer thickness [μm] | | 2 | 2 | 2 | 2 | 1.5 | 1.5 |
| Color [L*a*b*] | | | | | | ND | ND |
| L* | | 98.1 | 97.4 | 98.4 | 98.9 | | |
| a* | | −0.5 | −0.3 | −0.19 | −0.11 | | |
| b* | | +3.8 | +4.6 | +2.5 | +1.5 | | |
| Silver content [wt %] | | 100 | 100 | 100 | 100 | 100 | 100 |
| Electrolyte stability (observation 4) | | a | a | a | a | a | a |

| | | Example no. | | | | | |
|---|---|---|---|---|---|---|---|
| Component | Concentration | 19 | 20 | 21 | 22 | 23 | 24 |
| Silver (as silver methanesulfonate) | g/l | 0 | 20 | 20 | 20 | 20 | 20 |
| Silver (as silver nitrate) | g/l | 0 | 0 | 0 | 0 | 0 | 0 |
| Silver (as silver oxide) | g/l | 10 | 0 | 0 | 0 | 0 | 0 |
| Silver (as silver hydantoin complex) | g/l | 0 | 0 | 0 | 0 | 0 | 0 |
| Tin (as potassium hexahydroxostannate(IV)) | g/l | 0 | 0 | 0 | 0 | 0 | 0 |
| Palladium (as palladium(II) bis(ethylenediamine) sulfate) | g/l | 0 | 0 | 0 | 0 | 0 | 0 |
| Rhodium (as rhodium(III) sulfate) | g/l | 0 | 0 | 0 | 0 | 0 | 0 |
| Potassium nitrate | g/l | 0 | 0 | 0 | 0 | 0 | 0 |
| Potassium chloride | g/l | 0 | 0 | 0 | 0 | 0 | 0 |
| Potassium methanesulfonate | g/l | 0 | 0 | 0 | 0 | 0 | 0 |
| Hydantoin | g/l | 0 | 0 | 0 | 0 | 0 | 0 |
| 5,5'-Dimethylhydantoin | g/l | 60 | 150 | 150 | 150 | 150 | 150 |
| 5,5'-Diethylhydantoin | g/l | 0 | 0 | 0 | 0 | 0 | 0 |
| Glycine | g/l | 40 | 0 | 20 | 0 | 0 | 0 |
| 2,2'-Sulfanediyldiethanol | g/l | 0 | 0 | 0 | 0 | 0 | 0 |
| Tetrahydro-2H-1,4-thiazine | ml/l | 0 | 0.2 | 0.2 | 0.2 | 0.2 | 0.2 |
| Cysteine | g/l | 0 | 0 | 0 | 0 | 0 | 0 |
| Beta-alanine | g/l | 0 | 0 | 0 | 0 | 0 | 0 |
| Methionine | g/l | 0.25 | 0 | 0 | 0 | 0 | 0 |
| Proline | g/l | 0 | 0 | 0 | 0 | 0 | 150 |
| Sarcosine | g/l | 0 | 0 | 0 | 115 | 115 | 0 |
| L-Glutamic acid | g/l | 0 | 0 | 195 | 0 | 0 | 0 |
| Toluenesulfonamide | g/l | 0 | 0 | 0 | 0 | 0 | 0 |
| Mercaptonicotinic acid | g/l | 0 | 0 | 0 | 0 | 0 | 0 |
| Picolylamine | ml/l | 0 | 0 | 0 | 0 | 0 | 0 |
| Nicotinic acid | g/l | 0 | 0 | 0 | 0 | 20 | 0 |
| Nicotinamide | g/l | 0 | 0 | 0 | 0 | 0 | 0 |
| Parameters/observations | | | | | | | |
| pH | | 9.6 | 9.6 | 9.6 | 9.6 | 9.6 | 9.6 |
| Temperature [° C.] | | 60 | 65 | 65 | 65 | 65 | 65 |
| Current density [A/dm2] | | 0.1-0.7 | 0.1-0.4 | 0.1-1 | 0.1-3 | 0.1-3 | 0.1-1 |
| Movement (observation 1) | | d | d | d | d | d | d |
| Anode (observation 2) | | a | a | a | a | a | a |
| Appearance (observation 3) | | a | a | a | a | a | a |
| Layer thickness [μm] | | 1.5 | 1.5 | 1.5 | 1.5 | 1.5 | 1.5 |
| Color [L*a*b*] | | ND | ND | ND | | ND | ND |
| L* | | | | | 98.7 | | |
| a* | | | | | −0.2 | | |
| b* | | | | | 1.7 | | |

TABLE 1-continued

| | | | | | | |
|---|---|---|---|---|---|---|
| Silver content [wt %] | 100 | 100 | 100 | 100 | 100 | 100 |
| Electrolyte stability (observation 4) | a | a | a | a | a | a |

Observation 1:
a Glass beaker (60 mm stirrer bar; 200 rpm), cathode movement
b Glass beaker (60 mm stirrer bar; 200 rpm), barrel
c Jet plating (400 l/h)
d Hull cell (stirrer bar 40 mm; 600 rpm)

Observation 2:
a Silver anode
b Platinized titanium
c Mixed metal oxide

Observation 3:
a Homogeneous, white, glossy
b Homogeneous, white, matte
c Yellowish Observation 4:
a No precipitation, stable for months, constant quality of the coatings
b No precipitation, but no constant quality of the coatings possible
c Precipitation after a short time
ND not determined

TABLE 2

Exemplary embodiments according to the invention

| Component | Concentration | Example no. 25 | 26 | 27 | 28 | 29 |
|---|---|---|---|---|---|---|
| Silver (as silver methanesulfonate) | g/l | 0 | 0 | 40 | 0 | 20 |
| Silver (as silver nitrate) | g/l | 0 | 30 | 0 | 5 | 0 |
| Silver (as silver oxide) | g/l | 20 | 0 | 0 | 0 | 0 |
| Silver (as silver hydantoin complex) | g/l | 0 | 0 | 0 | 0 | 0 |
| Nickel (as nickel(II) sulfate heptahydrate) | g/l | 0 | 0 | 0 | 0 | 0 |
| Tin (as potassium hexahydroxostannate(IV)) | g/l | 0 | 0 | 0 | 0 | 0 |
| Palladium (as palladium(II) bis(ethylenediamine) sulfate) | g/l | 0 | 0 | 0 | 0 | 0 |
| Rhodium (as rhodium(III) sulfate) | g/l | 0 | 0 | 0 | 0 | 0 |
| Potassium nitrate | g/l | 0 | 0 | 0 | 0 | 0 |
| Potassium chloride | g/l | 0 | 0 | 0 | 0 | 0 |
| Potassium methanesulfonate | g/l | 0 | 0 | 0 | 0 | 0 |
| Hydantoin | g/l | 7 | 0 | 0 | 0 | 0 |
| 5,5'-Dimethylhydantoin | g/l | 125 | 150 | 120 | 40 | 125 |
| 5,5'-Diethylhydantoin | g/l | 0 | 0 | 0 | 0 | 0 |
| Glycine | g/l | 40 | 60 | | 10 | 40 |
| Tetrahydro-2H-1,4-thiazine | ml/l | 0 | 0 | 0 | 0 | 0 |
| Cysteine | g/l | 0.5 | 0.25 | 0.2 | 0.25 | 0.3 |
| 4-Amino-N-(2-pyrimidinyl)benzenesulfonamide | g/l | 0 | 0 | 0 | 0 | 0 |
| 4-Amino-N-(1,3-thiazol-2-yl)benzenesulfonamide | g/l | 0.1 | 0 | 0 | 0 | 0 |
| 4-Aminobenzenesulfonamide | g/l | 0 | 1.0 | 0 | 0.5 | 0 |
| 4-Amino-N-(diaminomethylene)benzenesulfonamide | g/l | 0 | 0 | 0 | 0 | 0.1 |
| Polyethyleneimine (Lupasol FG) | ml/l | 0 | 0 | 0.1 | 0 | 0 |
| Trans-3-(3-pyridyl)acrylic acid | g/l | 0 | 0 | 1 | 0 | 0 |
| Beta-alanine | g/l | 0 | 0 | 0 | 0 | 0 |
| Methionine | g/l | 0 | 0 | 0 | 0 | 0 |
| Proline | g/l | 0 | 0 | 0 | 0 | 0 |
| Sarcosine | g/l | 0 | 0 | 0 | 0 | 0 |
| Nicotinic acid | g/l | 0 | 0 | 100 | 0 | 0 |
| Nicotinamide | g/l | 0 | 0 | 0 | 0 | 0 |
| Parameters/observations | | | | | | |
| pH | | 9.2 | 9.5 | 9.8 | 8.8 | 9.6 |
| Temperature [° C.] | | 50 | 60 | 60 | 45 | 50 |
| Current density [A/dm2] | | 0.25-2.0 | 0.5-5.0 | 0.5-10.0 | 0.1-1.0 | 0.25-2.0 |
| Movement (observation 1) | | a | d | c | b | b |
| Anode (observation 2) | | a | a | b | a | a |
| Appearance (observation 3) | | c | a,b | a | a | a |
| Layer thickness [μm] | | 2 | 2 | 2 | 0.2 | 10 |

TABLE 2-continued

| | | | | | |
|---|---|---|---|---|---|
| Color [L*a*b*] | | ND | | | |
| L* | | 96.6 | 98.4 | 98.1 | 98 |
| a* | | −1.6 | −0.3 | −0.4 | −0.4 |
| b* | | 10.3 | 5.8 | 3.3 | 3.5 |
| Silver content [wt %] | | | | | |
| Electrolyte stability (observation 4) | | a | a | a | a |

| | | Example no. | | | | |
|---|---|---|---|---|---|---|
| Component | Concentration | 30 | 31 | 32 | 33 | 34 |
| Silver (as silver methanesulfonate) | g/l | 0 | 0 | 30 | 0 | 0 |
| Silver (as silver nitrate) | g/l | 40 | 0 | 0 | 40 | 0 |
| Silver (as silver oxide) | g/l | 0 | 20 | 0 | 0 | 0 |
| Silver (as silver hydantoin complex) | g/l | 0 | 0 | 0 | 0 | 40 |
| Nickel (as nickel(II) sulfate heptahydrate) | g/l | 0 | 0 | 0 | 0 | 0 |
| Tin (as potassium hexahydroxostannate(IV)) | g/l | 0 | 0 | 0 | 0 | 0 |
| Palladium (as palladium(II) bis(ethylenediamine) sulfate) | g/l | 0 | 0 | 0 | 0 | 0 |
| Rhodium (as rhodium(III) sulfate) | g/l | 0 | 0 | 0 | 0 | 0 |
| Potassium nitrate | g/l | 0 | 0 | 0 | 0 | 0 |
| Potassium chloride | g/l | 0 | 0 | 0 | 0 | 0 |
| Potassium methanesulfonate | g/l | 0 | 0 | 10 | 0 | 0 |
| Hydantoin | g/l | | | | | |
| 5,5'-Dimethylhydantoin | g/l | 120 | 125 | 125 | 120 | 0 |
| 5,5'-Diethylhydantoin | g/l | 0 | 0 | 0 | 0 | 120 |
| Glycine | g/l | 0 | 0 | 40 | 0 | 0 |
| Tetrahydro-2H-1,4-thiazine | ml/l | 0 | 0.2 | 0 | 0 | 0 |
| Cysteine | g/l | 0.25 | 0 | 0.3 | 0.25 | 0.25 |
| 4-Amino-N-(2-pyrimidinyl)benzenesulfonamide | g/l | 0.5 | 0 | 0.5 | 0 | 0 |
| 4-Amino-N-(1,3-thiazol-2-yl)benzenesulfonamide | g/l | 0 | 0 | 0 | 0 | 0 |
| 4-Aminobenzenesulfonamide | g/l | 0 | 0.25 | 0 | 0 | 2 |
| 4-Amino-N-(diaminomethylene)benzenesulfonamide | g/l | 0 | 0.1 | 0 | 0.2 | 0 |
| Polyethyleneimine (Lupasol FG) | ml/l | 0.05 | 0 | 0 | 0 | 0 |
| Trans-3-(3-pyridyl)acrylic acid | g/l | 0 | 0 | 0 | 0 | 0 |
| Beta-alanine | g/l | 0 | 40 | 0 | 0 | 0 |
| Methionine | g/l | 0 | 0 | 1 | 0 | 0 |
| Proline | g/l | 0 | 0 | 0 | 0 | 0 |
| Sarcosine | g/l | 0 | 0 | 10 | 0 | 0 |
| Nicotinic acid | g/l | 100 | 0 | 0 | 0 | 50 |
| Nicotinamide | g/l | 0 | 0 | 0 | 100 | 50 |
| Parameters/observations | | | | | | |
| pH | | 9.5 | 9 | 9.6 | 9.5 | 9.5 |
| Temperature [° C.] | | 60 | 50 | 60 | 60 | 60 |
| Current density [A/dm2] | | 1-10 | 0.25-3.0 | 1-5 | 0.5-5 | 0.5-3 |
| Movement (observation 1) | | c | a | d | d | d |
| Anode (observation 2) | | b | a | a | a | a |
| Appearance (observation 3) | | a | a | a | a | a |
| Layer thickness [μm] | | 2 | 10 | 2 | 2 | 2 |
| Color [L*a*b*] | | | | ND | ND | ND |
| L* | | 98.2 | 98 | | | |
| a* | | −0.4 | −0.2 | | | |
| b* | | 4.2 | 2.6 | | | |
| Silver content [wt %] | | 100 | 100 | 100 | 100 | 100 |
| Electrolyte stability (observation 4) | | a | a | a | a | a |

| | | Example no. | | | | |
|---|---|---|---|---|---|---|
| Component | Concentration | 35 | 36 | 37 | 38 | 39 |
| Silver (as silver methanesulfonate) | g/l | 10 | 0 | 10 | 20 | 0 |
| Silver (as silver nitrate) | g/l | 0 | 0 | 0 | 0 | 20 |
| Silver (as silver oxide) | g/l | 0 | 0 | 0 | 0 | 0 |
| Silver (as silver hydantoin complex) | g/l | 0 | 10 | 0 | 0 | 0 |
| Nickel (as nickel(II) sulfate heptahydrate) | g/l | 0 | 0 | 0 | 1 | 0 |

TABLE 2-continued

| | | | | | | |
|---|---|---|---|---|---|---|
| Tin (as potassium hexahydroxostannate(IV)) | g/l | 30 | 0 | 0 | 0 | 0 |
| Palladium (as palladium(II) bis(ethylenediamine)sulfate) | g/l | 0 | 5 | 0 | 0 | 0 |
| Rhodium (as rhodium(III) sulfate) | g/l | 0 | 0 | 6 | 0 | 0 |
| Potassium nitrate | g/l | 0 | 0 | 0 | 0 | 10 |
| Potassium chloride | g/l | 8 | 8 | 8 | 0 | 0 |
| Potassium methanesulfonate | g/l | 0 | 0 | 0 | 0 | 0 |
| Hydantoin | g/l | 0 | 0 | 0 | 0 | 0 |
| 5,5'-Dimethylhydantoin | g/l | 50 | 0 | 50 | 0 | 150 |
| 5,5'-Diethylhydantoin | g/l | 0 | 50 | 0 | 50 | 0 |
| Glycine | g/l | 0 | 0 | 0 | 20 | 0 |
| Tetrahydro-2H-1,4-thiazine | ml/l | 0 | 0 | 0 | 0 | 0.2 |
| Cysteine | g/l | 0 | 0 | 0 | 0.5 | 0 |
| 4-Amino-N-(2-pyrimidinyl)benzenesulfonamide | g/l | 0 | 0 | 0 | 0 | 0 |
| 4-Amino-N-(1,3-thiazol-2-yl)benzenesulfonamide | g/l | 0 | 0 | 0 | 0 | 0 |
| 4-Aminobenzenesulfonamide | g/l | 0 | 0 | 0 | 1 | 0 |
| 4-Amino-N-(diaminomethylene)benzenesulfonamide | g/l | 0 | 0 | 0 | 0 | 0 |
| Polyethyleneimine (Lupasol FG) | ml/l | 0 | 0 | 0 | 0 | 0 |
| Trans-3-(3-pyridyl)acrylic acid | g/l | 0 | 0 | 0 | 0 | 0 |
| Beta-alanine | g/l | 0 | 0 | 0 | 0 | 0 |
| Methionine | g/l | 0 | 0 | 0 | 0 | 0 |
| Proline | g/l | 0 | 0 | 0 | 0 | 150 |
| Sarcosine | g/l | 0 | 0 | 0 | 0 | 0 |
| Nicotinic acid | g/l | 0 | 0 | 0 | 0 | 0 |
| Nicotinamide | g/l | 0 | 0 | 0 | 0 | 0 |
| Parameters/observations | | | | | | |
| pH | | 12.1 | 9.5 | 12.8 | 9.5 | 10 |
| Temperature [° C.] | | 40 | 40 | 40 | 50 | 65 |
| Current density [A/dm2] | | 1 | 2 | 1 | 1 | 0.1-1 |
| Movement (observation 1) | | a | a | a | a | d |
| Anode (observation 2) | | a | a | a | a | a |
| Appearance (observation 3) | | b,c gray | a, gray | a | a | a |
| Layer thickness [μm] | | 2.1 | 1.8 | 2.4 | 2 | 1.5 |
| Color [L*a*b*] | | | | | | ND |
| L* | | 54.3 | 74.7 | 80.9 | 95.8 | |
| a* | | +2.8 | −0.8 | −1.7 | −0.6 | |
| b* | | +15.1 | −1.4 | +4.3 | 7.3 | |
| Silver content [wt %] | | 96.3 | 92.1 | 93.9 | 98.3 | |
| Electrolyte stability (observation 4) | | a | a | a | a | a |

Observation 1:
a Glass beaker (60 mm stirrer bar; 200 rpm), cathode movement
b Glass beaker (60 mm stirrer bar; 200 rpm), barrel
c Jet plating (400 l/h)
d Hull cell (stirrer bar 40 mm; 600 rpm)
Observation 2:
a Silver anode
b Platinized titanium
c Mixed metal oxide
Observation 3:
a Homogeneous, white, glossy
b Homogeneous, white, matte
c Yellowish
Observation 4:
a No precipitation, stable for months, constant quality of the coatings
b No precipitation, but no constant quality of the coatings possible
c Precipitation after a short time
ND not determined

TABLE 3

Comparative examples

| | | Example no. | | | |
|---|---|---|---|---|---|
| Component | Concentration | 1 | 2 | 3 | 4 |
| Silver (as silver methanesulfonate) | g/l | 0 | 0 | 30 | 0 |
| Silver (as silver nitrate) | g/l | 0 | 0 | 0 | 16 |
| Silver (as silver hydantoin complex) | g/l | 0 | 0 | 0 | 0 |

TABLE 3-continued

| Component | | | | |
|---|---|---|---|---|
| Silver (as silver oxide) | g/l | 40 | 40 | 0 | 0 |
| Potassium chloride | g/l | 0 | 0 | 0 | 8 |
| Amidosulfonic acid | g/l | 35 | 35 | 0 | 0 |
| Hydantoin | g/l | 0 | 0 | 0 | 0 |
| 5,5'-Dimethylhydantoin | g/l | 117.5 | 117.5 | 80 | 50 |
| Thiosalicylic acid | g/l | 0 | 0 | 0 | 1 |
| Potassium methanesulfonate | g/l | 0 | 0 | 150 | 0 |
| Imidosuccinate, sodium salt | g/l | 0 | 0 | 0 | 0 |
| 2,2'-Sulfanediyldiethanol | g/l | 2 | 2 | 0 | 0 |
| 3-Trans-(3-pyridyl)acrylic acid | g/l | 4 | 4 | 0 | 0 |
| Tripotassium citrate monohydrate | g/l | 0 | 0 | 0 | 0 |
| Naphthalenesulfonic acid-formaldehyde polycondensate | g/l | 0 | 0 | 15 | 0 |
| Sulfopropylated polyalkoxylated naphthol, potassium salt | g/l | 0 | 0 | 2.5 | 0 |
| Polyethylene glycol octyl (3-sulfopropyl) diether, potassium salt | g/l | 0 | 0 | 0 | 0 |
| Potassium nitrate | g/l | 15 | 15 | 0 | 0 |
| Parameters/observations | | | | | |
| pH | | 9.5 | 9.6 | 9.8 | 9.5 |
| Temperature [° C.] | | 60 | 60 | 55 | 50 |
| Current density [A/dm2] | | 5 | 1 | 1 | 1.5 |
| Movement (observation 1) | | c | c | a | a |
| Anode (observation 2) | | a | a | a | a |
| Appearance (observation 3) | | a,b | c | b,c | c |
| Layer thickness [μm] | | 1.5 | 1.5 | 1 | 2 |
| Color [L*a*b*] | | | | | |
| L* | | 97.1 | 96.4 | 68.7 | 87.5 |
| a* | | −0.5 | −0.6 | −0.7 | −2.7 |
| b* | | +5.6 | +6.4 | +7.1 | +14.2 |
| Silver content [wt %] | | 100 | 100 | 100 | 100 |
| Electrolyte stability (observation 4) | | a | a | c | c |

| | | | Example no. | | |
|---|---|---|---|---|---|
| | Component | Concentration | 5 | 6 | 7 |
| | Silver (as silver methanesulfonate) | g/l | 0 | 0 | 30 |
| | Silver (as silver nitrate) | g/l | 16 | 0 | 0 |
| | Silver (as silver hydantoin complex) | g/l | 0 | 0 | 0 |
| | Silver (as silver oxide) | g/l | 0 | 11 | 0 |
| | Potassium chloride | g/l | 8 | 8 | 0 |
| | Amidosulfonic acid | g/l | 0 | 0 | 0 |
| | Hydantoin | g/l | 40 | 40 | 0 |
| | 5,5'-Dimethylhydantoin | g/l | 0 | 0 | 130 |
| | Thiosalicylic acid | g/l | 0 | 0 | 0 |
| | Potassium methanesulfonate | g/l | 0 | 0 | 0 |
| | Imidosuccinate, sodium salt | g/l | 0 | 0 | 10 |
| | 2,2'-Sulfanediyldiethanol | g/l | 0 | 0 | 0 |
| | 3-Trans-(3-pyridyl)acrylic acid | g/l | 0 | 0 | 0 |
| | Tripotassium citrate monohydrate | g/l | 0 | 0 | 40 |
| | Naphthalenesulfonic acid-formaldehyde polycondensate | g/l | 0 | 0 | 0 |
| | Sulfopropylated polyalkoxylated naphthol, potassium salt | g/l | 0 | 0 | 0 |
| | Polyethylene glycol octyl (3-sulfopropyl) diether, potassium salt | g/l | 0 | 0 | 0 |
| | Parameters/observations | | | | |
| | pH | | 9.5 | 9 | 10.3 |
| | Temperature [° C.] | | 40 | 45 | 40 |
| | Current density [A/dm2] | | 1 | 1 | 2 |
| | Movement (observation 1) | | a | a | c |
| | Anode (observation 2) | | a | a | a |
| | Appearance (observation 3) | | c, matte | c, matte | b |
| | Layer thickness [μm] | | 1 | 1 | 2 |
| | Color [L*a*b*] | | ND | ND | ND |
| | L* | | | | |
| | a* | | | | |
| | b* | | | | |

TABLE 3-continued

| | | | |
|---|---|---|---|
| Silver content [wt %] | 100 | 100 | 100 |
| Electrolyte stability (observation 4) | b | b | c |

Observation 1:
a Glass beaker (60 mm stirrer bar; 200 rpm), cathode movement
b Glass beaker (60 mm stirrer bar; 200 rpm), barrel
c Glass beaker (60 mm stirrer bar; 400 rpm), cathode movement
d Jet plating (400 l/h)

Observation 2:
a Silver anode
b Platinized titanium
c Mixed metal oxide

Observation 3:
a Homogeneous, white, glossy
b Homogeneous, white, matte
c Yellowish Observation 4:
a No precipitation, stable for months, constant quality of the coatings
b No precipitation, but no constant quality of the coatings possible
c Precipitation after a short time
ND = not determined

| | | |
|---|---|---|
| Comparative example 1 | U.S. 2012/0067733 A1 | Example 4 |
| Comparative example 2 | U.S. 2012/0067733 A1 | Example 4 |
| Comparative example 3 | U.S. 2016/0122890 A1 | Example 1 |
| Comparative example 4 | U.S. Pat. No. 5,601,696 | Example 5 |
| Comparative example 5 | U.S. Pat. No. 5,601,696 | Example 1 |
| Comparative example 6 | U.S. Pat. No. 5,601,696 | Example 2 |
| Comparative example 7 | U.S. 2011/0062030 | Example 1 |

Determination of Color Values

Color values were measured according to the L*a*b color space for a silver layer deposited from an electrolyte according to the invention and for three comparative examples.

Experimental Conditions:
Volumes: 1 liter
Magnetic stirrer: IKA RET CV
Stirring: 200 and 400 rpm; the higher stirring rate was used at current densities above 3 A/dm².
Stirrer bar: 60 mm
Cathode: moved parallel to anodes, 5 cm/s
Cathode surface: 0.2 dm², brass
Cathodic current density: 0.5 to 3 A/dm²
Layer thicknesses: 1.5 µm.
Anodes: 99.9% silver
Temperature: 40° C.-65° C., depending on the stability of the solution. Comparative example 4 was tested at 40° C. because more silver was deposited at 50° C. (original parameter of example 5 in U.S. Pat. No. 5,601,696) than is theoretically electrochemically possible. This is a sign that, in addition to galvanic deposition, chemical deposition also takes place, the latter being undesirable.
pH: 9.5 to 10, depending on the example.
Measuring instrument: Konica Minolta Spectrophotometer CM-700, SCI 10°/D65

Determination of the L* values

In the L*a*b* color space, the L* axis describes the lightness of the color with values from 0 (black) to 100 (white).

In each case, layers of 1.5 µm thickness were deposited at current densities of 0.5 to 3.0 A/dm₂.

| Current density [A/dm²] | L* value | | | |
|---|---|---|---|---|
| | Exemplary embodiment 1 | Comparative example 2 | Comparative example 3 | Comparative example 4 |
| 0.5 | 98.3 | 97.2 | 75.4 | 87.4 |
| 1.0 | 98.7 | 96.4 | 68.7 | 88.6 |
| 1.5 | 98.7 | 96.7 | | 87.5 |
| 2.0 | 98.7 | 96.9 | | 78.8 |
| 2.5 | 98.7 | 96.4 | | 78.8 |
| 3.0 | 98.8 | 97.2 | | 88.6 |

FIG. 1 shows the results of determining the L* values.

Determination of the a* Values

In the L*a*b* color space, the a* axis describes the green or red portion of a color, wherein negative values stand for green and positive values for red.

In each case, layers of 1.5 µm thickness were deposited at current densities of 0.5 to 3.0 A/dm².

| Current density [A/dm²] | a* value | | | |
|---|---|---|---|---|
| | Exemplary embodiment 1 | Comparative example 2 | Comparative example 3 | Comparative example 4 |
| 0.5 | −0.13 | −0.45 | −2.15 | −3.06 |
| 1.0 | −0.13 | −0.59 | −0.72 | −3.12 |
| 1.5 | −0.09 | −0.65 | | −2.65 |
| 2.0 | −0.08 | −0.39 | | −0.31 |
| 2.5 | −0.10 | −0.65 | | −3.12 |
| 3.0 | −0.07 | −0.39 | | −0.31 |

Figure 2:
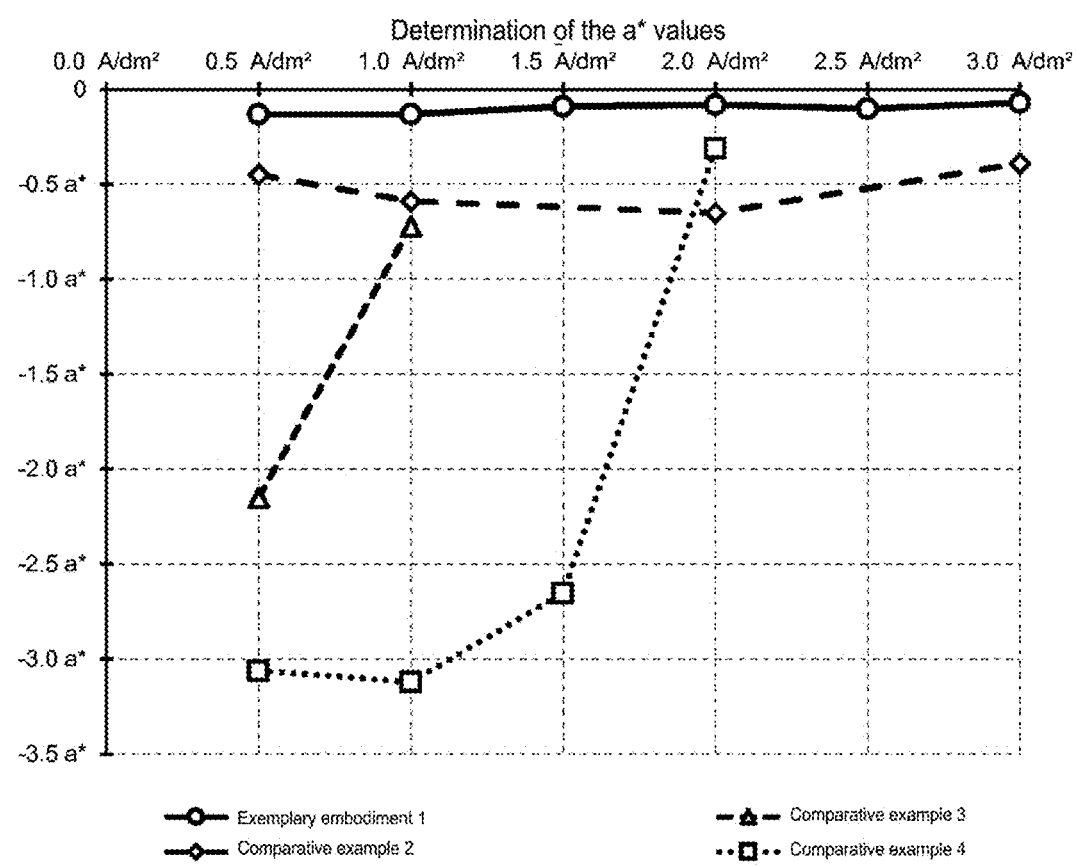
FIG. 2 shows the results of determining the a* values of deposited layers.

FIG. 2 shows the results of determining the a* values.

Determination of the b* Values

In the L*a*b* color space, the b* axis describes the blue or yellow portion of a color, wherein negative values stand for blue and positive values for yellow.

In each case, layers of 1.5 µm thickness were deposited at current densities of 0.5 to 3.0 A/dm².

| Current density [A/dm$^2$] | b* value | | | |
|---|---|---|---|---|
| | Exemplary embodiment 1 | Comparative example 2 | Comparative example 3 | Comparative example 4 |
| 0.5 | +2.60 | +5.41 | +6.63 | +3.97 |
| 1.0 | +1.97 | +6.37 | +7.13 | +3.43 |
| 1.5 | +1.88 | +6.99 | | +14.21 |
| 2.0 | +1.74 | +5.11 | | +8.33 |
| 2.5 | +1.81 | +5.11 | | +3.43 |
| 3.0 | +1.54 | +6.99 | | +14.21 |

Figure 3:
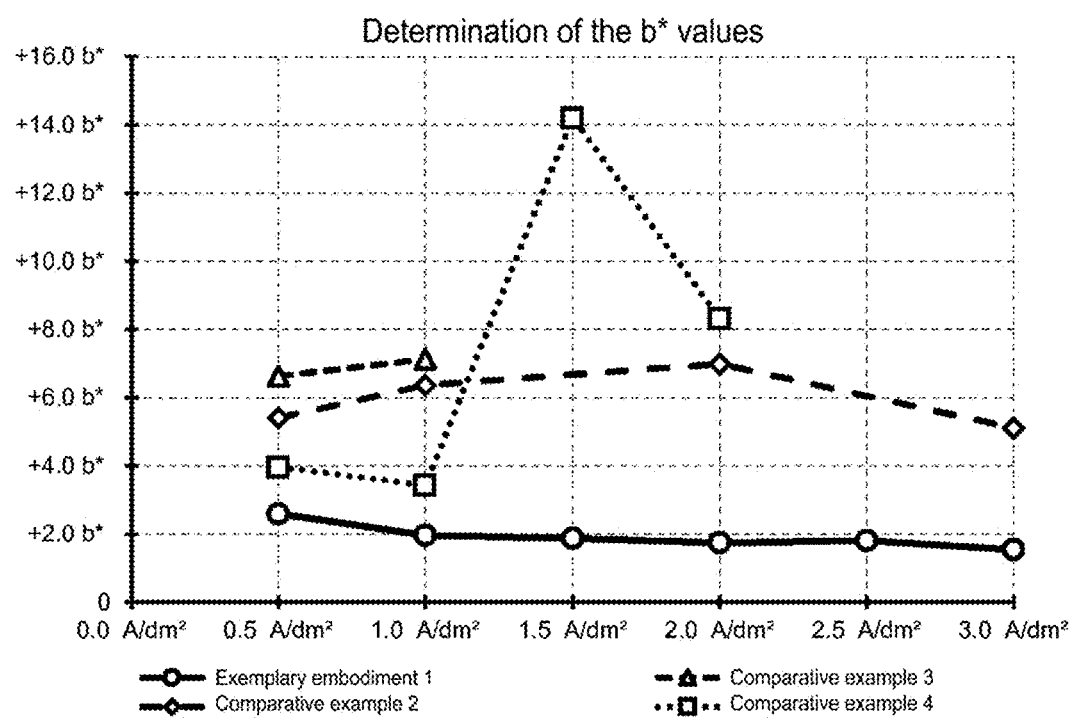
FIG. 3 shows the results of determining the b* values of deposited layers.

FIG. 3 shows the results of determining the b* values.

The invention claimed is:

1. An aqueous cyanide-free electrolyte for the electrolytic deposition of silver and silver alloy coatings, which has the following constituents in dissolved form:
   a) at least one silver compound in a concentration of 0.1-150 g/l silver,
   b) at least one compound of an alloy metal in a concentration of 0 to 100 g/l alloy metal,
   c) at least one compound of formula (I)

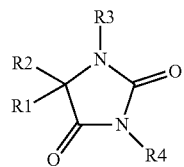

wherein
   R1, R2, R3 and R4 independently represent hydrogen, a linear or branched alkyl group having 1 to 5 carbon atoms, an alkoxy group having 1 to 5 carbon atoms, a hydroxyalkyl group having 1 to 5 carbon atoms or an aryl group,
   and
   wherein the at least one compound of formula (I) is present in a concentration of 1 to 350 g/l,
   d) at least one brightener carrier selected from i) at least one amino acid in a concentration of 0.0001-5 mol/l, in particular 0.01-5 mol/l, and/or ii) at least one pyridinecarboxylic acid in a concentration of 0.01-5 mol/l
   e) a brightening agent comprising or consisting of a sulfonamide having $R_1$—$SO_2$—$NR_2R_3$ as structural element, wherein $R_1$, $R_2$ and $R_3$ are, independently of one another, a ($C_1$-$C_{10}$) alkyl, a ($C_3$-$C_{10}$) cycloalkyl, a ($C_6$-$C_{10}$) aryl, a ($C_5$-$C_{10}$) heteroaryl, or a ($C_5$-$C_{10}$) heterocycloalkyl, wherein the concentration of the brightening agent is 0.005-25 g/l,
   f) an alkali metal hydroxide selected from lithium hydroxide, sodium hydroxide, potassium hydroxide and mixtures thereof in a concentration of 1-200 g/l,
   g) wherein the electrolyte has a pH of greater than or equal to 7.

2. The electrolyte according to claim 1, wherein the brightening agent further comprises 2,2'-sulfanediyldiethanol, cysteine, methionine, aliphatic and aromatic heterocyclic compounds having 5 to 7 ring atoms, wherein the ring of the aliphatic and aromatic heterocyclic compounds contains at least one heteroatom selected from nitrogen and sulfur, and wherein the aliphatic and aromatic heterocyclic compounds optionally contain one or more further heteroatoms selected from nitrogen, oxygen and sulfur, or mixtures thereof,
   wherein, if the brightening agent comprises cysteine and/or methionine and at least one brightening carrier according to d)i) the at least one amino acid is neither cysteine nor methionine.

3. The electrolyte according to claim 1, wherein the silver compound is selected from silver methanesulfonate, silver carbonate, silver phosphate, silver pyrophosphate, silver nitrate, silver oxide, silver lactate, silver fluoride, silver bromide, silver chloride, silver iodide, and silver sulfate.

4. The electrolyte according to claim 1, wherein the compound of the at least one alloy metal is selected from compounds of tin, palladium, antimony, cobalt, indium, iron, nickel, ruthenium, rhodium, platinum, copper, zinc, selenium, tellurium, bismuth, iridium, germanium, gallium, rhenium, tungsten, molybdenum, dysprosium, cerium, and gold.

5. The electrolyte according to claim 1, wherein the at least one compound of formula (I) is selected from 1-methylhydantoin, 1,3-dimethylhydantoin, 5,5-dimethylhydantoin, 1-hydroxymethyl-5,5-dimethylhydantoin, 5,5'-diethylhydantoin and 5,5-diphenylhydantoin, and mixtures thereof.

6. The electrolyte according to claim 1, wherein the at least one amino acid is selected from glycine, alanine, proline, sarcosine, and mixtures thereof.

7. The electrolyte according to claim 1, wherein the at least one pyridinecarboxylic acid is selected from picolinic acid, picolinic acid amide, nicotinic acid, nicotinamide, isonicotinic acid, isonicotinamide, and mixtures thereof.

8. A method for the electrolytic deposition of silver coatings and silver alloy coatings from an electrolyte according to claim 1, which comprises immersing an electrically conductive substrate in the electrolyte and a flow of current is established between an anode in contact with the electrolyte and the substrate as cathode.

9. The method according to claim 8, wherein the temperature of the electrolyte is 20° C. to 90° C.

10. The method according to claim 8, wherein the current density during electrolysis is 0.2 to 100 A/dm$^2$.

11. The method according to claim 8, which comprises adjusting the pH to range between 9 and 11 during the electrolysis.

12. The method according to claim 8, wherein a soluble silver anode and/or an insoluble anode is used as anode.

* * * * *